United States Patent [19]
Juan et al.

[11] Patent Number: 5,869,055
[45] Date of Patent: Feb. 9, 1999

[54] ANTI-INFLAMMATORY CD14 POLYPEPTIDES

[75] Inventors: Shao-Chieh Juan, Moorpark, Calif.; Henri S. Lichenstein, Boulder, Colo.; Samuel D. Wright, Westfield, N.J.

[73] Assignee: Amgen, Inc., Thousand Oaks, Calif.

[21] Appl. No.: 484,397

[22] Filed: Jun. 7, 1995

Related U.S. Application Data

[63] Continuation-in-part of Ser. No. 366,953, Dec. 30, 1994.
[51] Int. Cl.$^6$ .......... A01K 38/00; C07K 14/705; C07H 21/04
[52] U.S. Cl. .......... 424/185.1; 530/351; 530/300; 530/317; 536/23.5; 514/2
[58] Field of Search .......... 424/185.1; 530/351, 530/300, 317; 536/23.5; 514/2

[56] References Cited

FOREIGN PATENT DOCUMENTS

WO 91/01639  2/1991  WIPO.
WO 92/04908  4/1992  WIPO.
WO 93/19772  10/1993  WIPO.

OTHER PUBLICATIONS

Haziot et al. 1988 J. Immunology 141:547.
Ferrero et al. (1990) *The Journal of Immunology* 145:331–336.
Ferrero et al. (1988) *Nucleic Acids Research* 16:9.
Goyert et al. (1988) *Science* 239:497–500.
Juan et al. (1995) *The Journal of Biological Chemistry* 270: 1382–1387.
Pugin et al. (1994) *Immunity* 1:509–516.
Setoguchi et al. (1989) *Biochimica et aBiophysia Acta* 1008:213–222.
Vinyakosol et al. (1995) *The Journal of Biological Chemistry* 270:331–368.
Juan et al. (1995), 'Identification of a lipopolyaccharide binding domain in CD14 between amino acids 57 and 64', *J Bio Chem* 270(10):5219–5224.
Juan et al. (1995), 'Identification of a domain in sCD14 essential for Lipopolysaccharide (LPS) signaling but not LPS binding', *J. Bio Chem* 207(29):17237–17242.
McGinley et al. (1995), 'CD14: Physical properties and identification of an exposed site that is protected by Liopopolysaccharide', *J Bio Chem* 270(10):5213–5218.
Weinstein (1983), 'Chemistry and Biochemistry of Amino Acids, Peptides and Proteins', Marcel Dekker, Inc. 7:336–345.

*Primary Examiner*—Thomas M. Cunningham
*Assistant Examiner*—Martha T. Lubet
*Attorney, Agent, or Firm*—Timothy J. Gaul; Ron K. Levy; Steven M. Odre

[57] ABSTRACT

The invention relates to anti-inflammatory polypeptides comprising soluble CD14 related polypeptides having amino acids at position 7–10 that are different from the native sequence or having amino acids 1–14 deleted.

14 Claims, 12 Drawing Sheets

FIG. 2

Sequence and expression of sCD14 alanine-substitution mutants.

| Name | Sequence of mutant sCD14[1] | Expression in COS-7 cells[2] |
|---|---|---|
| 1. sCD14 1-348 | TTPEPCELDDEDFRCVCNFSEPQPDWSEAFQCVSAVEVEIHAGGLNLEPFLKRVDADADP | + |
| 2. sCD14 (7-10)A | ———AAAA——————————————————————————————————————————— | + |
| 3. sCD14 (11-14)A | ——————AAAA——————————————————————————————————————— | + |
| 4. sCD14 (18-21)A | —————————————AAAA———————————————————————————————— | − |
| 5. sCD14 (22-25)A | —————————————————AAAA———————————————————————————— | + |
| 6. sCD14 (26-28)A | —————————————————————AAA————————————————————————— | + |
| 7. sCD14 (30-31)A | —————————————————————————AA——————————————————————— | + |
| 8. sCD14 (45-48)A | ————————————————————————————————————————AAAA——————— | + |
| 9. sCD14 (49-52)A | ————————————————————————————————————————————AAAA—— | + |
| 10. sCD14 (53-55)A | ————————————————————————————————————————————————AAA | + |

1 Sequence between amino acids 1 and 60 from mature sCD14 are shown. Solid lines indicate the same sequences as sCD14 1-348.
2 Expression of sCD14 proteins in COS-7 cells was determined by Western blot using polyclonal anti-CD14 antiserum.

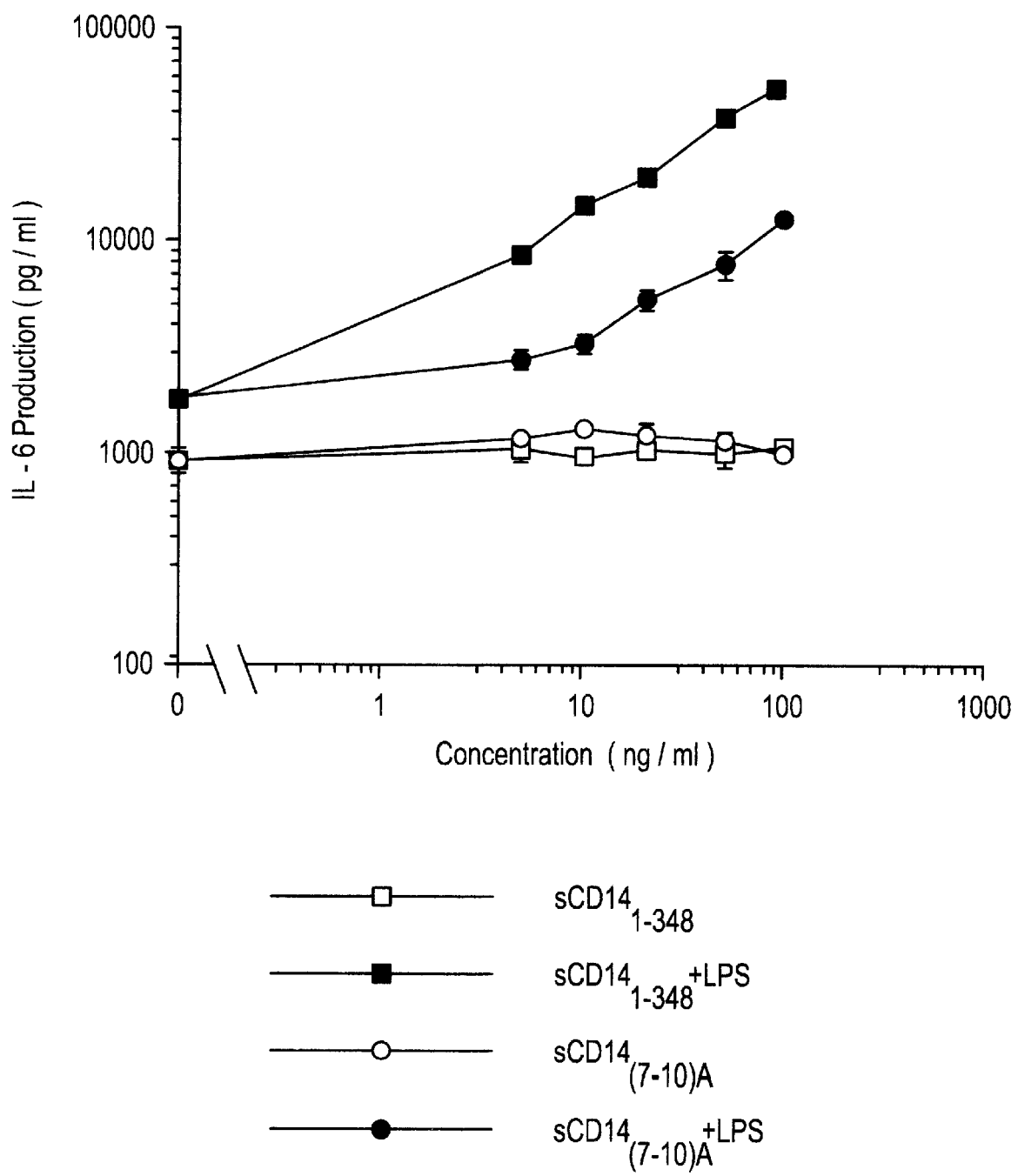

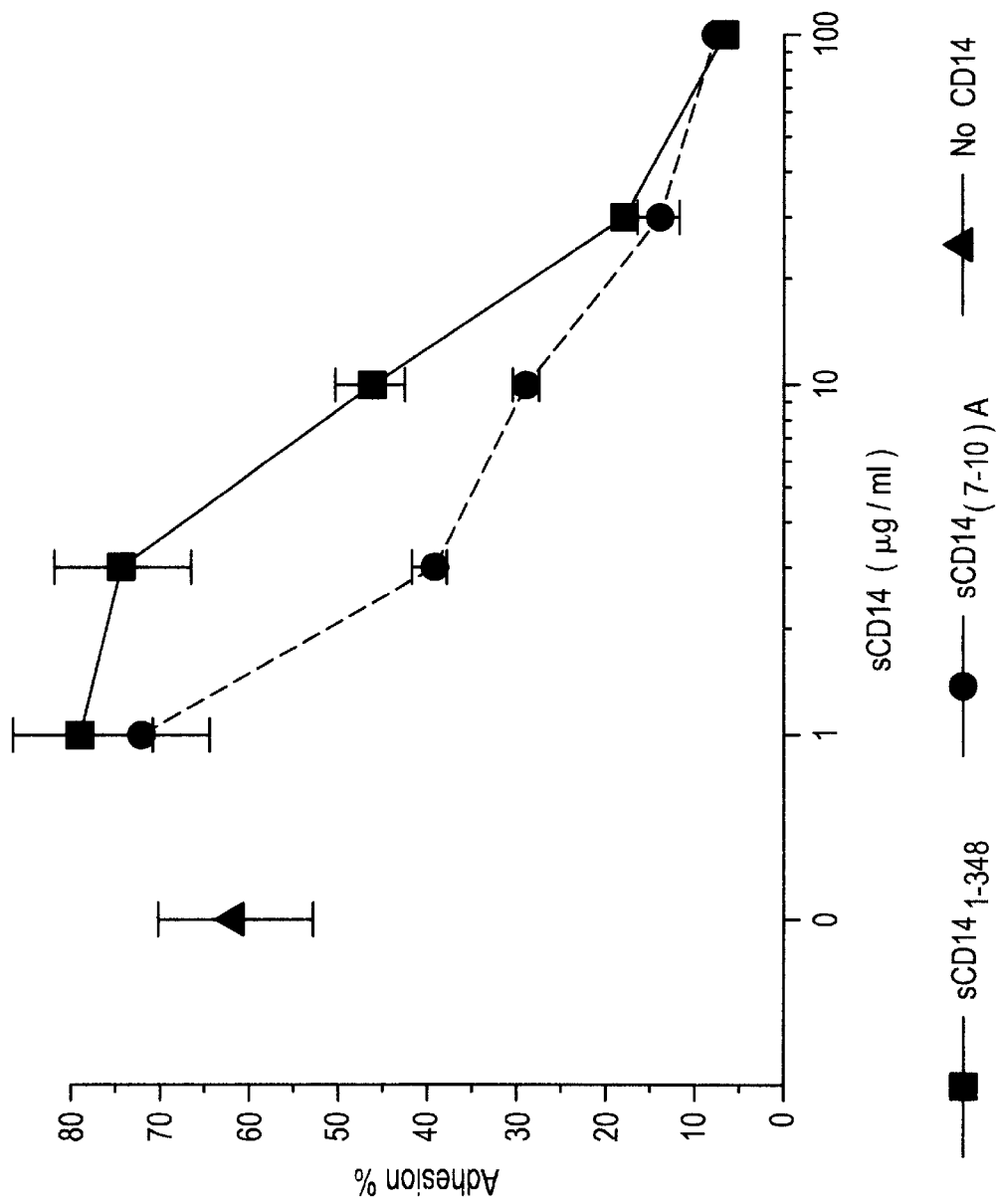

1

ANTI-INFLAMMATORY CD14 POLYPEPTIDES

This application is a continunation-in-part of application Ser. No. 08/366,953 filed Dec. 30, 1994.

FIELD OF THE INVENTION

Generally, the invention relates to the field of polypeptides that have anti-inflammatory properties. Amino acids 7 to 10 of CD14 have been found to contain an important domain enabling inflammatory responses in cells, including IL-6 production. The polypeptides of this invention were based on replacing amino acids 7–10 in the soluble form of CD14 with different amino acids. Other polypeptides of this invention are missing the first 14 amino acids of soluble CD14. The polypeptides of the invention may be used to treat inflammatory conditions, such as sepsis.

BACKGROUND OF THE INVENTION

Sepsis is a life-threatening medical condition that can be brought on by infection or trauma. The symptoms of sepsis can include chills, profuse sweating, fever, weakness, or hypotension, followed by leukopenia, intravascular coagulation, shock, adult respiratory distress syndrome, multiple organ failure, and often, death. R. Ulevitch, et al., *J. Trauma* 30: S189–92 (1990).

The lipopolysaccharides ("LPS"; also, "endotoxins") that are typically present on the outer membrane of all gram-negative bacteria are among the most studied and best understood sepsis-inducing substances. While the precise chemical structures of LPS molecules obtained from different bacteria may vary in a species-specific fashion, a region called the lipid A region is common to all LPS molecules. E. Rietschel et al., in *Handbook of Endotoxins*, 1: 187–214, eds. R. Proctor and E. Rietschel, Elsevier, Amsterdam (1984). This lipid A region is responsible for many, if not all, of the LPS-dependent pathophysiologic changes that characterize sepsis.

LPS is believed to be a primary cause of death in humans afflicted with gram-negative sepsis. van Deventer et al., *Lancet*, 1: 605 (1988); Ziegler et al., *J. Infect. Dis.*, 136: 19–28 (1987). Treatment of patients suffering from sepsis and gram-negative bacteraemia with a monoclonal antibody against LPS decreased their mortality rate. Ziegler et al., *N. Eng. J. Med.*, 324: 429 (1991).

Sepsis is also caused by gram-positive bacteria. Bone, R. C. Arch. *Intern, Med.*, 154: 26–34 (1994). The activation of host cells can originate from gram-positive cell walls or purified cell components such as peptidoglycan and lipoteichoic acid. Such substances induce a similar pattern of inflammatory responses to those induced by LPS. Chin and Kostura, *J. Immunol.* 151: 5574–5585 (1993); Mattson et al., *FEMS Immun. Med. Microbiol.* 7: 281–288 (1993); and Rotta, *J. Z. Immunol. Forsch. Bd.*: 149: 230–244 (1975).

LPS and gram-positive cell wall substances cause polymorphonuclear leukocytes, endothelial cells, and cells of the monocyte/macrophage lineage to rapidly produce and release a variety of cell products, including cytokines, which are capable of initiating, modulating or mediating humoral and cellular immune responses and processes.

One particular cytokine, alpha-cachectin or tumor necrosis factor (TNF-α), is apparently a primary mediator of septic shock. Beutler et al., *N. Eng. J. Med.*, 316: 379 (1987). Intravenous injection of LPS into experimental animals and man produces a rapid, transient release of TNF-α. Beutler et al., *J. Immunol.*, 135: 3972 (1985); Mathison et al., *J. Clin. Invest.* 81: 1925 (1988). Pretreatment of animals with anti-TNF-α antibodies can modulate septic shock. Beutler et al., *Science*, 229: 869, (1985); Mathison et al., *J. Clin. Invest.* 81: 1925 (1988).

Molecular receptors that can combine with sepsis-inducing substances, and that once combined, initiate certain chemical reactions, play a critical role in the etiology of the symptoms of sepsis. CD14 is a 55-kD glycoprotein expressed strongly on the surface of monocytes and macrophages, and weakly on the surface of granulocytes, such as neutrophils. S. M. Goyert et al., *J. Immunol.* 137: 3909 (1986). A. Haziot et al., *J. Immunol.* 141: 547–552 (1988); S. M. Goyert et al., *Science* 239: 497 (1988).

The cDNAs and the genes for human and murine CD14 have been cloned and sequenced. E. Ferrero and S. M. Goyert, *Nuc. Acids Res.* 16: 4173 (1988); S. M. Goyert et al., *Science* 239: 497 (1988); M. Setoguchi et al., *Biochem. Biophys. Acta* 1008: 213–22 (1989). CD14 is linked by a cleavable glycosyl phosphatidyl inositol tail [A. Haziot et al., *J. Immunol.* 141: 547–552 (1988)] to the exoplasmic surface of mature monocytes, macrophages, granulocytes and dendritic reticulum cells, or renal nonglomerular endothelium, and of hepatocytes in rejected livers.

CD14 mediates responses by binding to LPS. Complexes of LPS and sCD14 exhibit a 1:1 stoichiometry (Hailman, E., et al., *J. Exp. Med.* 179: 269–277 (1994)), and these complexes initiate TNF-α production in monocytes (Dentener, M. A., et al., *J. Immunol.* 7: 2885–2891 (1993)), IL-6 production in astrocytes (Frey, E., et al., *J. Exp. Med.* 176: 1665–1671 (1992)), production of adhesion molecules in endothelial cells (Frey, E., et al., *J. Exp. Med.* 176: 1665–1671 (1992)) and activation of leukocyte integrins in PMN (Hailman, E., et al., *J. Exp. Med.* 179: 269–277 (1994)). Spontaneous binding of LPS to CD14 is slow, but this binding may be dramatically accelerated by LBP. LBP acts in a catalytic fashion, with one molecule of LBP transferring hundreds of LPS molecules to hundreds of CD14 molecules.

Other experiments have shown that cell activation can also be induced by interaction of CD14 with components of gram-positive bacteria such as *B. subtilis, S. aureus,* and *S. mitus* (Pugin et al., *Immunity* 1: 509–516 (1994). Furthermore, interaction of CD14 with lipoarabinomannan from the cell wall of *Mycobacterium tuberculosis* also induces cellular activation in a CD14-dependent fashion (Zhang et al., *J. Clin. Invest.* 91: 2076–2083 (1993); Pugin et al., *Immunity* 1: 509–516 (1994)). These studies suggest that CD14 is a receptor which recognizes a wide variety of bacterial structures. Interaction of CD14 with these structures initiates host inflammatory responses.

Several neutralizing monoclonal antibodies (mAbs) to CD14 have been shown to antagonize cellular responses to LPS in vitro (Wright, S. D., et al. *Science* 249: 1431–1433 (1990); Hailman, E., et al. *J. Exp. Med.* 179, 269–277 (1994); Frey, E. A., et al. *J. Exp. Med.* 176, 1665–1671 (1992); Arditi, M., et al. *Infect. Immun.* 61, 3149–3156 (1993); Wright, S. D., et al. *J. Exp. Med.* 173, 1281–1286 (1991); Dentener, M. A., et al. *J. Immunol* 150, 2885–2891 (1993); Grunwald, U., et al. *J. Immunol Methods* 155, 225–232 (1992)) and in vivo (Leturcq, D. J., et al. *Satellite Meeting of the 3rd Conference of the International Endotoxin Society* 22 (Abstract) (1994)); and Wright, et al., *Science* 90: 1431–1433 (1990). Additional in vivo data have demonstrated that animals injected with CD14 neutralizing monoclonal antibodies become hyporesponsive to LPS and mice lacking CD14 fail to respond to LPS. These experiments suggest that the release of inflammatory cytokines can be blocked by preventing the interaction of LPS with membrane CD14.

CD14 has also been shown to exist as a soluble protein found in normal sera or urine of nephrotic patients. Recent evidence has shown that sCD14 enables LPS-dependent responses in cells which lack membrane CD14, i.e., endothelial cells and epithelial cells. In these cells types, sCD14 in conjunction with LPS promotes inflammatory cytokine release and upregulation of adhesion molecules.

Interestingly, high concentrations of sCD14 have been shown to block inflammatory cytokine release from monocytes in a whole blood assay. Presumably, the beneficial effect of sCD14 in this assay arises from its ability to divert LPS away from mCD14 on macrophages and PMNs. Thus sCD14, like CD14 neutralizing monoclonal antibodies, could be useful in preventing LPS interactions in mCD14. However, the utility of sCD14 to treat LPS-mediated inflammatory disorders is limited by its other property of eliciting inflammatory cytokines in endothelial cells. Thus, a sCD14 molecule which retained its ability to bind LPS, yet did not activate endothelial cells should have superior properties in treating inflammation.

Monoclonal antibodies may be a useful tool to help identify domains in sCD14 required for cell activation. We have demonstrated that mAbs MEM-18 and 3C10 recognize a sCD14 mutant truncated at amino acid 152, indicating that epitopes for these two mAbs are within the first 152 amino acids (Juan, T. S. -C., et al. *J. Biol. Chem.* 270, 1382–1387 (1995)). We further localized the epitope of MEM-18 between amino acids 57 and 64 and found that this region is also essential for LPS binding (Juan, T. S. -C., et al. *J. Biol. Chem.* 270, 5219–5224 (1995)). Deletion of this region not only disrupted binding of MEM-18, but also binding of LPS.

The epitope for mAb 3C10 defines another functional domain of CD14. This mAb appears to recognize a different region from that of MEM-18 (Juan, T. S. -C., et al. *J. Biol. Chem.* 270, 1382–1387 (1995)). Binding of monoclonal antibody 3C10 to sCD14 does not affect LPS binding to sCD14 (Juan, T. S. -C., et al. *J. Biol. Chem.* 270, 5219–5224 (1995)), suggesting that this epitope may be involved in a cellular function other than LPS binding.

For the preceding reasons, it is an object of this invention to develop methods and therapies for the effective treatment, including prevention, for symptoms of inflammatory conditions, including sepsis. It is also an object of this invention to develop methods and therapies for the effective protection of individuals who are at risk of becoming afflicted by the symptoms of inflammation, including sepsis.

It is another object of this invention to develop methods and therapies for the effective treatment, including prevention, of symptoms of diseases that are mediated by LPS, gram-negative bacteraemia, gram-positive cell components, gram-positive bacteraemia, mycobacterial lipoarabinomannan, mycobacterial infections and/or CD14. Such diseases include ARDS, septic shock, acute pancreatitis, acute and chronic liver failure, intestinal or liver transplantation, inflammatory bowel disease, graft vs. host disease in bone marrow transplantation and tuberculosis.

SUMMARY OF THE INVENTION

The present inventors have discovered a group of polypeptides that are capable of binding to lipopolysaccharide (LPS), resulting in inhibition of the binding of LPS or gram-positive cell components to membrane CD14, thus reducing or eliminating CD14-mediated inflammatory responses. As used herein, inhibition of binding of LPS also means inhibition of binding to gram-positive cell components. This group of polypeptides was designed by the inventors based on their important discovery of an LPS-binding domain in CD14.

The polypeptides of this invention are based on substituting the naturally-occurring amino acids at positions 7–10 of CD14, preferably in a soluble form, with neutral amino acids, preferably those having either a hydrogen or C1–C6 alkyl side chain. The polypeptides of this invention also include those that begin at amino acid 15 of FIG. 1. With reference to FIG. 1, "soluble" CD14 (sCD14) is a molecule selected from sequences starting at an amino acid of from 1 through 6 and ending at an amino acid of from 152 through 348. Native human CD14 has as $X_1$–$X_4$, Glu-Leu-Asp-Asp (SEQ ID NO:1) in FIG. 1. Preferably, the polypeptide is substituted with alanine at each of positions 7 through 10.

The polypeptides of this invention are capable of binding to LPS, thereby preventing further binding of microbial cell components to membrane CD14. If microbial cell interaction with membrane CD14 is prevented, the cascade of events leading to inflammation, and especially sepsis, are reduced or prevented. Therefore, the polypeptides of this invention have anti-inflammatory properties.

More specifically, the evidence provided herein indicates, inter alia, that a polypeptide having the region from amino acids 7 to 10 in CD14 replaced with alanine residues or having amino acids 1 to 14 deleted from soluble CD14, binds LPS but mediates a substantially reduced cellular inflammatory response, such as production of the cytokine IL-6 in response to LPS, as compared to native CD14.

In the examples below, we identify the epitope of 3C10 by making a series of site-directed alanine substitution mutants in sCD14. We show that the region between amino acids 7 and 14 are required for 3C10 binding. We further characterized this domain by generating a sCD14 mutant with alanine substituted at amino acids 7 to 10 (sCD14$_{(7-10)A}$). This mutant was capable of binding LPS but was impaired in its ability to mediate cellular responses to LPS.

The peptides and polypeptides of this invention may be prepared by (a) standard synthetic methods, (b) derivation from CD14, (c) recombinant methods, (d) a combination of one or more of (a)–(c), or other methods of preparing polypeptides.

The polypeptides of this invention may be used for therapeutic or prophylactic purposes by incorporating them into appropriate pharmaceutical carrier materials and administering an effective amount to a patient, such as a human (or other mammal) in need thereof.

BRIEF DESCRIPTION OF THE FIGURES

Numerous other aspects and advantages of the present invention will therefore be apparent upon consideration of the following detailed description thereof, reference being made to the drawings wherein:

FIG. 2 shows the sequence and expression of sCD14 (SEQ ID NO:2) alanine-substitution mutants.

FIG. 5 shows that sCD14$_{(7-10)A}$ is defective in enabling cellular responses to LPS. FIG. 5A. sCD14$_{(7-10)A}$ has reduced ability to stimulate IL-6 production by U373 cells. U373 cells were treated with various concentrations of sCD14$_{1-348}$ or sCD14$_{(7-10)A}$ in the presence or absence of LPS (20 ng/ml) for 24 h. IL-6 levels were determined as described (Juan, T. S. -C., et al. J. Biol. Chem. 270, 1382–1387 (1995)). Data presented are means ± standard deviations from four readings in an experiment repeated 3 times.

DETAILED DESCRIPTION OF THE PREFERRED EMBODIMENTS

The present invention is based on the discovery by the present inventors of a region on CD14 that is involved in inflammatory cellular responses mediated by CD14, such as production of IL-6 in response to gram negative or gram positive bacteria cell components (e.g., LPS from gram negative bacteria). The Examples below explain in detail the evidence supporting these discoveries.

Figure 1:
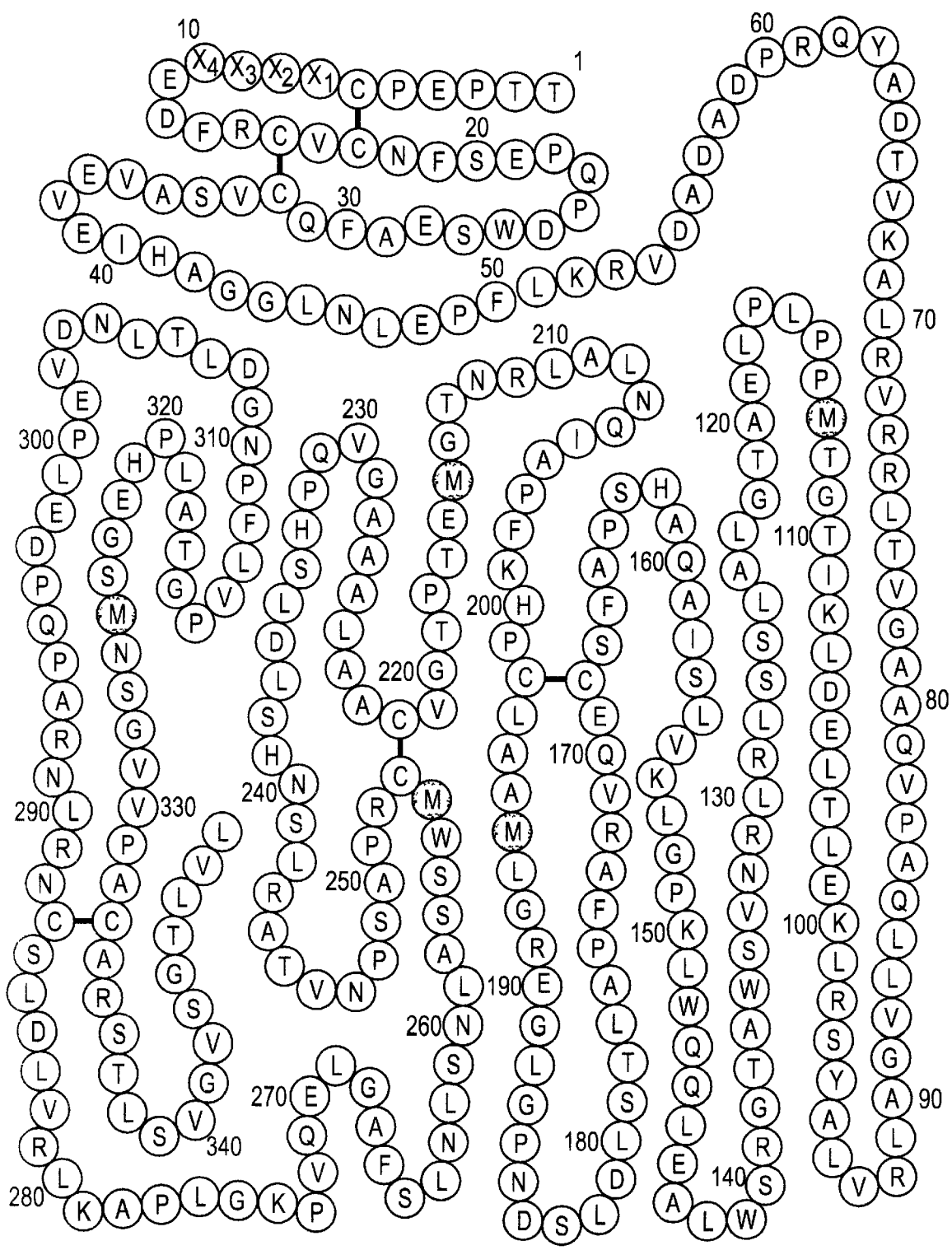
FIG. 1 (SEQ ID NO:38) shows a schematic map of soluble human CD14 having 348 amino acids (SEQ ID NO:27); amino acids 7–10 (shown as $X_1$–$X_4$) are Glu-Leu-Asp-Asp in native mature human CD14. In the polypeptides of this invention, amino acids 7–10 may be any of the amino acids described herein.

FIG. 1 shows a map of human CD14, including the LPS binding and IL-6 inducing region, corresponding to amino acids 7 to 10.

The polypeptides of this invention are based on substituting amino acids at positions 7–10, inclusive, in soluble CD14, with amino acids that are different from those in the native molecule or deleting the first 14 amino acids in soluble CD14. Referring to FIG. 1, amino acids 7–10 in the polypeptides that contain substituted amino acids, are different from Glu-Leu-Asp-Asp. Preferably, the substituted amino acids are neutral amino acids. The side chains of these neutral amino acids are preferably selected from the group consisting of hydrogen and alkyl groups having from 1 to 6 carbon atoms, which may be substituted by one or more substituents selected from halogen (e.g., Cl, Br, I), —OH, —CN, —OR (R=alkyl having 1 to 6 carbon atoms), and related structures. The specific amino acids substituted at amino acids 7–10 are relatively unimportant as long as the resulting polypeptide is capable of binding LPS and/or inhibiting release of inflammatory mediators in monocytes and PMNs while at the same time possessing a diminished ability (compared to wild type sCD14) to induce an inflammatory response in endothelial cells and epithelial cells. The polypeptides of this invention that have the initial 14 amino acids deleted from soluble CD14 end at an amino acid in sCD14 of from 152 to 348, inclusive. Preferred deletion-type peptides are amino acids 15–152 and 15–348 of FIG. 1.

The remainder of the polypeptide (other than the substituted amino acids) is generally identical to native soluble CD14. "Soluble CD14" (sCD14) means polypeptides that correspond to amino acids of from positions 1 through 6 to positions 152 through 348, of FIG. 1. Note that in all cases herein the numbering of amino acids used herein corresponds to the amino acids sequence of FIG. 1. For example, even if the particular soluble CD14 starts with the second through sixth amino acid as set forth in FIG. 1, the amino acids to be substituted are those corresponding to amino acids 7–10 of the full sequence of FIG. 1.

For purposes of this disclosure, the molecule depicted in FIG. 1 will be referred to as sCD14 or $sCD14_{1-348}$. Other examples of soluble CD14 will be named by providing the beginning and ending amino acids based on the numbering scheme of FIG. 1; e.g., $sCD14_{1-152}$; $sCD14_{2-152}$; $sCD14_{15-152}$; $sCD14_{15-348}$; etc. Polypeptides having amino acids substituted for those set forth in FIG. 1 will be named as follows: $sCD14_{1-348}$ having alanine in place of amino acids 7–10 in FIG. 1 is named $sCD14_{1-348(7-10)A}$, where "A" is the one-letter code for the amino acid alanine. $sCD14_{1-348}$ having an alanine at positions 7 and 9–10, and a glycine at position 8 is named $sCD14_{1-348(7, 9, 10)A(8)G}$.

Some specific preferred examples of polypeptides of this invention are set forth below:

---

$sCD14_{1-348(7-10)G}$ (SEQ ID NO. 2)    $sCD14_{1-152(7-10)G}$ (SEQ ID NO. 9)
$sCD14_{1-348(7-10)A}$ (SEQ ID NO. 3)    $sCD14_{1-152(7-10)A}$ (SEQ ID NO. 10)
$sCD14_{1-348(7-10)V}$ (SEQ ID NO. 4)    $sCD14_{1-152(7-10)V}$ (SEQ ID NO. 11)
$sCD14_{1-348(7-10)L}$ (SEQ ID NO. 5)    $sCD14_{1-152(7-10)L}$ (SEQ ID NO. 12)
$sCD14_{1-348(7-10)I}$ (SEQ ID NO. 6)    $sCD14_{1-152(7-10)I}$ (SEQ ID NO. 13)
$sCD14_{1-348(7-10)P}$ (SEQ ID NO. 7)    $sCD14_{1-152(7-10)P}$ (SEQ ID NO. 14)
$sCD14_{15-348}$ (SEQ ID NO. 8)    $sCD14_{15-152}$ (SEQ ID NO. 15)

---

The present invention also encompasses physiologically acceptable salts of the polypeptides disclosed herein. Also, in each polypeptide, one or more D or L amino acids may be included; however, it is preferred that all of the amino acids are of the L stereochemistry.

The polypeptides of this invention are expected to have the ability to reduce inflammatory responses in cells as compared to native sCD14. Reduction in inflammation may conveniently be measured by examining IL-6 production by such cells using, e.g., the method described in Example 4 below. Preferably the amount of IL-6 reduction, as compared to native sCD14, will be at least 5-fold, particularly preferably, at least 10-fold.

Also, in each case, the amino acids may be chemically derivatized as long as LPS binding coupled with reduced ability to induce IL-6 (or related cytokines) is retained. Thus, "chemical derivatives" of the present polypeptides are included within the scope of the term "polypeptide" as used herein. These chemical derivatives contain additional chemical moieties not part of the $X_1$–$X_4$ amino acid substituted polypeptides.

Covalent modifications of the polypeptides are included within the scope of this invention. Such modifications may be introduced into the molecule by reacting targeted amino acid residues of the polypeptide with an organic derivatizing agent that is capable of reacting with selected side chains or terminal residues.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK a of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptides or their functional derivatives to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

The activity of the polypeptide variant can be screened in a suitable screening assay for the desired characteristic. Biological activity is screened in an appropriate bioassay, as described herein. For example, binding of LPS to CD14 (or a polypeptide of this invention) may be measured in a standard competitive binding assay. Activity to reduce cellular inflammatory responses may be measured in terms of reduction of IL-6 production by cells (e.g., U373 cells) as described herein.

Modifications of such polypeptide properties as redox or thermal stability, hydrophobicity, susceptibility to proteolytic degradation or the tendency to aggregate with carriers or into multimers are assayed by methods well known to the ordinarily skilled artisan.

Such derivatized moieties may improve the solubility, absorption, biological half life, and the like. The moieties may alternatively eliminate or attenuate any undesirable side effect of the protein and the like. Moieties capable of mediating such effects are disclosed, for example, in Remington's Pharmaceutical Sciences, 16th ed., Mack Publishing Co., Easton, Pa. (1980).

The polypeptides of the invention may also be covalently or noncovalently associated with a carrier molecule, such as a polypeptide or non-CD14 protein, a linear polymer (such as polyethylene glycol, polylysine, etc), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct., 1993); a lipid; a cholesterol group (such as a steroid; or a carbohydrate or oligosaccharide.

The polypeptides of this invention are expected to have the ability to bind to LPS. This binding renders LPS unable to bind to membrane CD14 (mCD14) on macrophages and therefore produces an anti-inflammatory response in a mammal. Additionally, the polypeptides of this invention have reduced ability to trigger an inflammatory response in cells lacking mCD14 such as endothelial and epithelial cells. They are also expected to bind to cellular components of gram positive cells that cause inflammation (analogous to LPS; however, the structure(s) in gram positive bacteria that cause inflammatory responses to cells is (are) not yet known).

"Binding" to LPS means that in a standard competition assay, the polypeptide is capable of inhibiting 50% binding of CD14 to LPS between 1 mM and 1 nM, preferably 100 μm to 10 nM ($IC_{50}$ values). A standard binding assay may be carried out as is well known in the art.

The polypeptides of this invention may be made in a variety of ways. For example, solid phase synthesis techniques may be used. Suitable techniques are well known in the art, and include those described in Merrifield, in *Chem. Polypeptides*, pp. 335–61 (Katsoyannis and Panayotis eds. 1973); Merrifield, *J. Am. Chem. Soc.*, 85, 2149 (1963); Davis et al., *Biochem. Int'l*, 10, 394–414 (1985); Stewart and Young, *Solid Phase Peptide Synthesis* (1969); U.S. Pat. No. 3,941,763; Finn et al., in *The Proteins*, 3rd ed., vol. 2, pp. 105–253 (1976); and Erickson et al. in *The Proteins*, 3rd ed., vol. 2, pp. 257–527 (1976).

More preferably, the polypeptides are made in transformed host cells using recombinant DNA techniques. To do so, a recombinant DNA molecule coding for the polypeptide is prepared. Methods of preparing such DNA molecules are well known in the art. For instance, sequences coding for the polypeptides could be excised from DNA using suitable restriction enzymes. Alternatively, the DNA molecule could be synthesized using chemical synthesis techniques, such as the phosphoramidite method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity to it of the peptides encoded for by the DNA molecule, rate of transformation, ease of recovery of the peptides, expression characteristics, bio-safety and costs. A balance of these factors must be struck with the understanding that not all hosts may be equally effective for the expression of a particular DNA sequence.

Within these general guidelines, useful microbial hosts include bacteria (such as *E. coli* sp.), yeast (such as *Saccharomyces sp.*) and other fungi, insects, plants, mammalian (including human) cells in culture, or other hosts known in the art.

Next, the transformed host is cultured under conventional fermentation conditions so that the desired peptides are expressed. Such fermentation conditions are well known in the art.

Finally, the polypeptides are purified from the culture. These purification methods are also well known in the art.

The polypeptides of this invention may be used in any of a number of situations where LPS/gram positive cell component binding is required. For example, therapeutically and prophylactically, the polypeptides may be used for inflammatory bowel disease, acute and chronic liver failure, graft vs. host disease (bone marrow transplant), intestinal or liver transplant, ARDS, acute pancreatitis and tuberculosis. Septic shock is a particularly preferred target condition.

The novel polypeptides are useful for the prophylaxis or treatment of septic shock in mammals, including humans, at doses of about 0.1 to 100 mg/kg of body weight, preferably at a level of about 1 to 50 mg/kg of body weight, and the amount may be administered, e.g., in divided doses on daily basis. The polypeptides may be administered prophylactically to patients who may be exposed to or have been exposed to organisms which may cause septic shock or to detoxify LPS (bacterial endotoxins) by the use of the same dose set forth above in vivo; in vitro detoxification or prevention of endotoxin contamination may be carried out at a level which is effective to achieve the desired result. The amount may be based on routine experimentation based on the premise that about 1 mole of endotoxin is bound by 1 mole of polypeptide. The particular dose of a particular polypeptide may be varied within or without the range that is specified herein depending on the particular application or severity of a disease and the condition of the host. Those who are skilled in the art may ascertain the proper dose using standard procedures.

The pharmaceutical compositions of the present invention may be administered by any means that achieve their intended purpose. For example, administration may be by parenteral routes, including subcutaneous, intravenous, intradermal, intramuscular, intraperitoneal, intrathecal, transdermal, or buccal routes. Alternatively, or concurrently, administration may be by the oral or rectal route. The pharmaceutical compositions can be administered parenterally by bolus injection or by gradual perfusion over time.

In addition to the polypeptide, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to about 99 percent, preferably from about 25–85 percent, of active compound(s), together with the excipient.

Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethyl cellulose, and/or polyvinylpyrrolidone. If desired, disintegrating agents may also be added, such as the above-mentioned starches as well as carboxymethyl starch, cross-linked polyvinyl pyrrolidone, agar, or alginic acid or a salt thereof, such as sodium alginate. Auxiliaries which can be used in the compositions according to the present invention include flow-regulating agents and lubricants such as silica, talc, stearic acid or salts thereof, a detergent such as Triton, and/or polyethylene glycol.

It is understood that the application of the teachings of the present invention to a specific problem or situation will be within the capabilities of one having ordinary skill in the art in light of the teachings contained herein. Examples of the products of the present invention appear below.

EXAMPLES

Materials and Methods

Reagents.

Recombinant soluble CD14 (rsCD14) and recombinant LBP (rLBP) were constructed and purified as described (Hailman, E., et al. *J. Exp. Med.* 179, 269–277 (1994)). Concentrations of all purified proteins were determined with a Micro BCA protein kit (Pierce, Rockford, Ill.) according to manufacturer's specification. Since full-length rsCD14 terminates at position 348 of the mature protein (Hailman, E., et al. *J. Exp. Med.* 179, 269–277 (1994)), we herein refer it as sCD14$_{1-348}$. The anti-CD14 mAb 3C10 was purified by chromatography on Protein G from the conditioned medium (CM) of a cell line from American Type Culture Collection (ATCC TIB 228). Rabbit polyclonal anti-human CD14 antiserum was prepared as described (Juan, T. S. -C., et al. *J. Biol. Chem.* 270, 1382–1387 (1995)). Rough LPS (*Salmonella minnesota* R60 or Re595) and smooth LPS (*E. coli* 0111:B4 or *Salmonella minnesota* wild-type) were purchased from LIST Biological Laboratories (Campbell, Calif.). Enzymes for DNA manipulation were purchased from Boehringer Mannheim (Indianapolis, Ind.).

Site-directed mutagenesis.

Nine alanine-substitution mutants of sCD14 were used in this study. FIG. 2 summarizes the names and the amino acid residues substituted in each mutant. The Transformer site-directed mutagenesis kit (Clontech, Palo Alto, Calif.) was used as previously described (Juan, T. S. -C., et al. *J. Biol. Chem.* 270, 5219–5224 (1995)) to generate cDNAs encoding alanine-substitution mutants of sCD14 cloned in a mammalian expression vector. The primers used for each mutant are as follows:

5'-CGCCAGAACCTTGTGCAGCTGCCGCTGAAGATT-TCCGCTGC-3' (SEQ ID NO.16) for sCD14$_{(7-10)A}$, 5'-GTGAGCTGGACGATGCAGCTGCCGCCTGCGTCT-GCAACTTC-3' (SEQ ID NO.17) for sCD14$_{(11-14)A}$, 5'-CCGCTGCGTCTGCGCAGCTGCCGCACCTCAGCC-CGACTGG-3' (SEQ ID NO.18) for sCD14$_{(18-21)A}$, 5'-GCAACTTCTCCGAAGCAGCTGCCGCCTGGTCCG-AAGCCTTC-3' (SEQ ID NO.19) for sCD14$_{(22-25)A}$, 5'-GAACCTCAGCCCGACGCAGCTGCAGCCTTCCA-GTGTGTG-3' (SEQ ID NO.20) for sCD14$_{(26-28)A}$, 5'-CCGACTGGTCCGAAGCAGCTGCGTGTGTGTCT-GCAGTAGAG-3' (SEQ ID NO.21) for sCD14$_{(30-31)A}$, 5'-CATGCCGGCGGTGCAGCTGCAGCGCCGTTTCTA-AAGCGCG-3' (SEQ ID NO.22) for sCD14$_{(45-48)A}$, 5'-GGTCTCAACCTAGAGGCAGCTGCAGCGCGCGT-CGATGCGGAC-3' (SEQ ID NO.23) for sCD14$_{(49-52)A}$, and 5'-GAGCCGTTTCTAAAGGCAGCTGCTGCGGACGC-CGACCCG-3' (SEQ ID NO.24) for sCD14$_{(52-55)A}$.

Transient Expression of Mutant sCD14 Proteins in COS-7 Cells.

To express mutant sCD14 proteins, mammalian expression vectors containing mutant sCD14 cDNAs were introduced into COS-7 (ATCC CRL 1651) cells by electroporation. Conditions for electroporation and generation of serum-free CM from transfected COS-7 cells were as described (Juan, T. S. -C., et al. *J. Biol. Chem.* 270, 1382–1387 (1995)). Expression of mutant sCD14 was analyzed by Western blot using anti-CD14 polyclonal antibody.

BIAcore Analyses of Interactions Between sCD14 Mutants and 3C10 mAb.

Recognition of sCD14 mutant proteins by neutralizing monoclonal antibody 3C10 was performed with a BIAcore biosensor instrument. The instrument, CM5 sensor chips, and amine coupling kit were purchased from Pharmacia Biosensor (Piscataway, N.J.). Briefly, mAb 3C10 (200 µg/ml in 20 mM sodium acetate, pH 3.4) was immobilized to a CM5 sensor chip by amine coupling according to manufacturer's specifications. The flow cell immobilized with 3C10 was then incubated in succession with solutions as detailed in the following steps: Step 1, COS-7 CM for 2 min and Step 2, HBS buffer [10 mM N-2-hydroxyethylpiperazine-N'-2-ethanesulfonic acid, pH 7.5, 0.15M NaCl, 3.4 mM EDTA, 0.005% (V/V) surfactant P20 (Pharmacia Biosensor)] for 2 min. For regeneration, 10 mM HCl solution was injected for 2 min. Injection was performed at a rate of 5 µl/min. To quantitate the binding of sCD14 mutants in COS-7 CM to immobilized 3C10, we calculated relative a response unit (RRU). RRU was obtained by subtracting the response unit (RU) recorded just before injection of CM from the RU recorded after injection of CM and a 2 min wash.

Purification of sCD14$_{(7-10)A}$.

The expression vector containing the cDNA encoding sCD14$_{(7-10)A}$ was stably transfected into Chinese hamster ovary (CHO) cells deficient in dihydrofolate reductase as described (Hailman, E., et al. *J. Exp. Med.* 179, 269–277 (1994)). A single clone was grown without serum to generate CM containing sCD14$_{(7-10)A}$. Mutant protein was purified exactly as described (Juan, T. S. -C., et al. *J. Biol. Chem.* 270, 5219–5224 (1995)) except immunoaffinity chromatography was performed with anti-CD14 polyclonal antibody coupled to Sepharose 4B (Pharmacia, Piscataway, N.J.). Purity of the sample was checked by SDS-polyacrylamide gel electrophoresis (SDS-PAGE) followed by silver staining or Coomassie Blue staining. The changed amino acid sequence was verified through N-terminal sequencing.

U373 bioassays.

Growth of U373 cells (ATCC HTB17, Rockville, Md.), activation by purified sCD14 preparations, and quantitation of IL-6 were performed exactly as described (Juan, T. S. -C., et al. *J. Biol. Chem.* 270, 1382–1387 (1995)). Briefly, mixtures of $sCD14_{1-348}$ or $sCD14_{(7-10)A}$ and LPS were added to monolayers of U373 cells in serum—free medium and incubated for 24 h. IL-6 in the supernatant was then measured by ELISA.

Polymorphonuclear Leukocytes (PMN) Adhesion Assays.

The ability of rLBP and $sCD14_{(7-10)A}$ or $sCD14_{1-348}$ to enable PMN adhesion to fibrinogen-coated plates was assessed by previously established protocols (Hailman, E., et al. *J. Exp. Med.* 179, 269–277 (1994); Juan, T. S. -C., et al. *J. Biol. Chem.* 270, 1382–1387 (1995)). Briefly, PMN were incubated for 10 min with LPS, rLBP, and $sCD14_{(7-10)A}$ or $sCD14_{1-348}$, washed and adhesion to fibrinogen-coated surfaces was measured as described (Hailman, E., et al. *J. Exp. Med.* 179, 269–277 (1994); Juan, T. S. -C., et al. *J. Biol. Chem.* 270, 1382–1387 (1995)). When smooth LPS is used in this protocol, adhesion is completely dependent on addition of $sCD14_{1-348}$ (Juan, T. S. -C., et al. *J. Biol. Chem.* 270, 1382–1387 (1995)).

The ability of $sCD14_{(7-10)A}$ or $sCD14_{1-348}$ at high concentrations to bind LPS and inhibit LPS-mediated PMN adhesion was also assessed. In this experiment, rough LPS (*Salmonella minnesota* R60, 10 ng/ml) was incubated with rLBP (1 μg/ml) and the indicated concentrations of $sCD14_{(7-10)A}$ or $sCD14_{1-348}$ for 30 min at 37° C. before the addition of PMNs. The adhesion of PMNs was measured as described above.

Electrophoretic Mobility Shift Assays.

Whole cell extracts from U373 cells were prepared to assess transcription factor NF-κB activation. Cells were seeded in 6-well plates at a density of 1 million cells per well one day prior to stimulation. For stimulation, purified $sCD14_{1-348}$, $sCD14_{A(57-64)}$ (Juan, T. S. -C., et al. *J. Biol. Chem.* 270, 5219–5224 (1995)), or $sCD14_{(7-10)A}$ was added at a final concentration of 20 ng/ml with or without 20 ng/ml of Re595 LPS for 20 h. Cells were washed twice with 1× PBS (GIBCO-BRL), and scraped in 200 μl of lysis buffer (20 mM HEPES, pH 7.9, 20% glycerol, 0.1M KCl, 1 mM EDTA, 0.5 mM dithiothreitol, 1 mM Pefabloc (Boehringer Mannheim), 5 μg/ml Leupeptin, 1 mM sodium orthovanadate, and 2 μg/ml aprotinin) supplemented with 1% Triton X-100 (Sigma). Crude extracts were transferred to microfuge tubes and debris was separated by centrifugation at 14,000×g for 10 min at 4° C. Extracts were quickly frozen in liquid nitrogen and stored at −80° C. Protein concentration of the whole cell extracts were determined by micro BCA assay and ranged between 1.5–2 μg/μl.

For examining the NF-κB complexes, we performed electrophoretic mobility shift assays. Two oligonucleotides:

5'-CATGGAGGGACTTTCCGCTGGGGACTTTCC-AGC-3' (SEQ ID NO.25) and

5'-CATGGCTGGAAAGTCCCCAGCGGAAAGTC-CCTC-3' (SEQ ID NO.26)

were annealed to generate a double-stranded DNA containing the NF-κB binding site of human immunodeficiency virus long terminal repeat promoter (Nabel, G. and Baltimore, D. *Nature* 326, 711–713 (1987)). This annealed DNA fragment was then filled in with Klenow fragment (Boehringer Mannheim) and α-$^{32}$p dCTP (Amersham, Arlington Heights, Ill.) and used as probe at a concentration of 50,000 cpm per lane (about 25 fmole). For binding, 4 μl of whole cell extract was incubated with 4 μl of 5× binding buffer (150 mM Tris-HCl, pH 8.0, 40 mM $MgCl_2$, 5 mM DTT, and 10% glycerol), 2.5 μg of (poly dI-dC):(poly dI-dC) (Pharmacia, Piscataway, N.J.), radioactively labeled DNA probe and adequate amount of lysis buffer so that the final volume was 20 μl per reaction. The reactions were incubated in a 30° C. water bath for 30 min and complexes were resolved in a native 4.5% polyacrylamide gel using 0.5× TBE (50 mM Tris-HCl, pH 8.0, 45 mM boric acid, and 5 mM EDTA) at 30 mA for 2 h. The gel was then vacuum-dried at 80° C. for 1 h and exposed to Kodak X-ray film for 20 h. In competition experiments, 100× molar excess of unlabelled NF-κB probe was pre-incubated for 10 min before addition of radioactive probe.

Native PAGE Assays.

To directly assess LPS-binding of purified sCD14 preparations, $sCD14_{1-348}$ or $sCD14_{(7-10)A}$ were incubated at various concentrations (0, 101, 303, and 909 nM) with 3 μg/ml of $^3$H-LPS prepared from *E. coli* K12 strain LCD25 (List Biological Laboratories) in the presence or absence of 16.7 nM rLBP. The reaction was incubated at 37° C. for 30 min and then electrophoresed on native 4–20% polyacrylamide gels. Gels were prepared for fluorography as previously described (Hailman, E., et al. *J. Exp. Med.* 179, 269–277 (1994)).

Inhibition of LPS-Induced TNF-α Production in Whole Blood.

The ability of sCD14 to bind LPS and inhibit TNF-α production in whole blood has been described (Haziot, A., et al. *J. Immunol* 152, 5868–5876 (1994)). Briefly, various concentrations of bovine serum albumin (Miles, New Haven, Conn.), $sCD14_{1-348}$, or $sCD14_{(7-10)A}$ diluted in 50 μl RPMI medium (GIBCO-BRL, Gaithersburg, Md.) were added to 250 μl of freshly-drawn blood using heparin as an anti-coagulant. Smooth LPS (*Salmonella minnesota* wild-type) was added to a final concentration of 0.25 ng/ml. The reaction was incubated at 37° C. for 3 h and supernatants were obtained by centrifugation at 16,000×g for 2 min. TNF-α concentrations in the supernatants were assayed using a Quantikine TNF-α ELISA kit (R & D Systems, Minneapolis, Minn.) as suggested by the manufacturer.

Example 1

Alanine Substitution at amino acids 7 to 10 or 11 to 14 Disrupts Binding of Neutralizing mAb 3C10 to CD14.

3C10 is a mAb that recognizes the N-terminal 152 amino acid of CD14 (Juan, T. S. -C., et al. J. Biol. Chem. 270, 1382–1387 (1995)). Previous experiments have shown that 3C10 neutralizes the activity of $sCD14_{1-348}$ (Wright, S. D., et al. *Science* 249, 1431–1433 (1990); Hailman, E., et al. *J. Exp. Med.* 179, 269–277 (1994); Frey, E. A., et al. *J. Exp. Med.* 176, 1665–1671 (1992); Wright, S. D., et al. *J. Exp. Med.* 173, 1281–1286 (1991)). To verify that neutralization of sCD14 activity was due to binding of epitopes within the N-terminal 152 amino acids, we demonstrated that 3C10 inhibited IL-6 production in U373 cells mediated by either $sCD14_{1-348}$ or $sCD14_{1-152}$ (data not shown).

Figure 3:
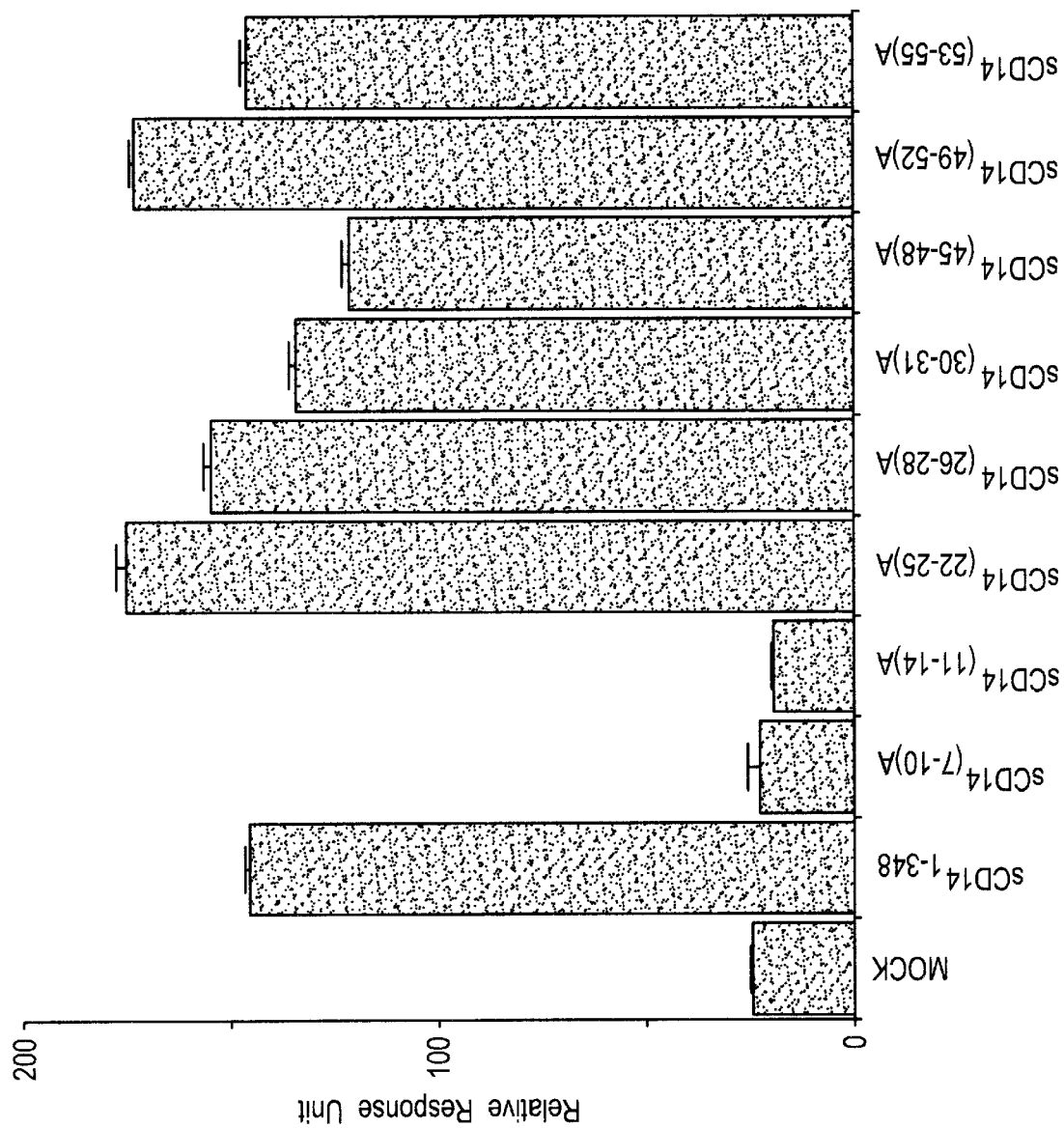
FIG. 3 shows the results of a BIAcore analysis of the monoclonal antibody 3C10 binding to alanine substitution mutants of sCD14. Conditioned media (CM) were collected from COS-7 cells transfected with no DNA (MOCK), sCD14$_{1-348}$, or sCD14 mutants four days after electroporation. All CM were analyzed for their ability to bind the antibody 3C10 as described in the Examples section herein. Relative response units (RRU) were recorded from four repeats of one experiment and calculated as means ± standard deviations.

To map the epitope for mAb 3C10, a series of alanine-substitution mutants were generated by site-directed mutagenesis (FIG. 2). Plasmids containing cDNA sequences encoding different sCD14 mutants were transfected into COS-7 cells and CM from these cells were examined for the expression of mutant sCD14 proteins by Western blot. With the exception of $sCD14_{(18-21)A}$, all sCD14 mutants were expressed and secreted by COS-7 cells (FIG. 2). BIAcore analysis (FIG. 3) was then used to examine the ability of CM containing mutant sCD14 to bind 3C10. CM containing $sCD14_{(7-10)A}$ or $sCD14_{(11-14)A}$ were found not to bind 3C10. These data suggest that the region between amino acids 7 and 14 is involved in recognizing 3C10.

Example 2
Purification and characterization of sCD14$_{(7-10)A}$.

Since neutralizing mAb 3C10 recognized amino acids 7 to 14, we reasoned that this region of CD14 could play an important role in the biological activity of CD14. To help understand the role of this region, we generated a stable CHO cell line expressing sCD14$_{(7-10)A}$ and purified mutant protein from the serum-free CM of this cell line. Purified sCD14$_{(7-10)A}$ migrated with an apparent Mr of 55,000 when analyzed by reducing SDS-PAGE (data not shown). N-terminal sequencing confirmed that the amino acids between 7 and 10 were replaced with alanines residues.

Example 3
mAb 3C10 Does not Recognize purified sCD14$_{(7-10)A}$.

Figure 4:
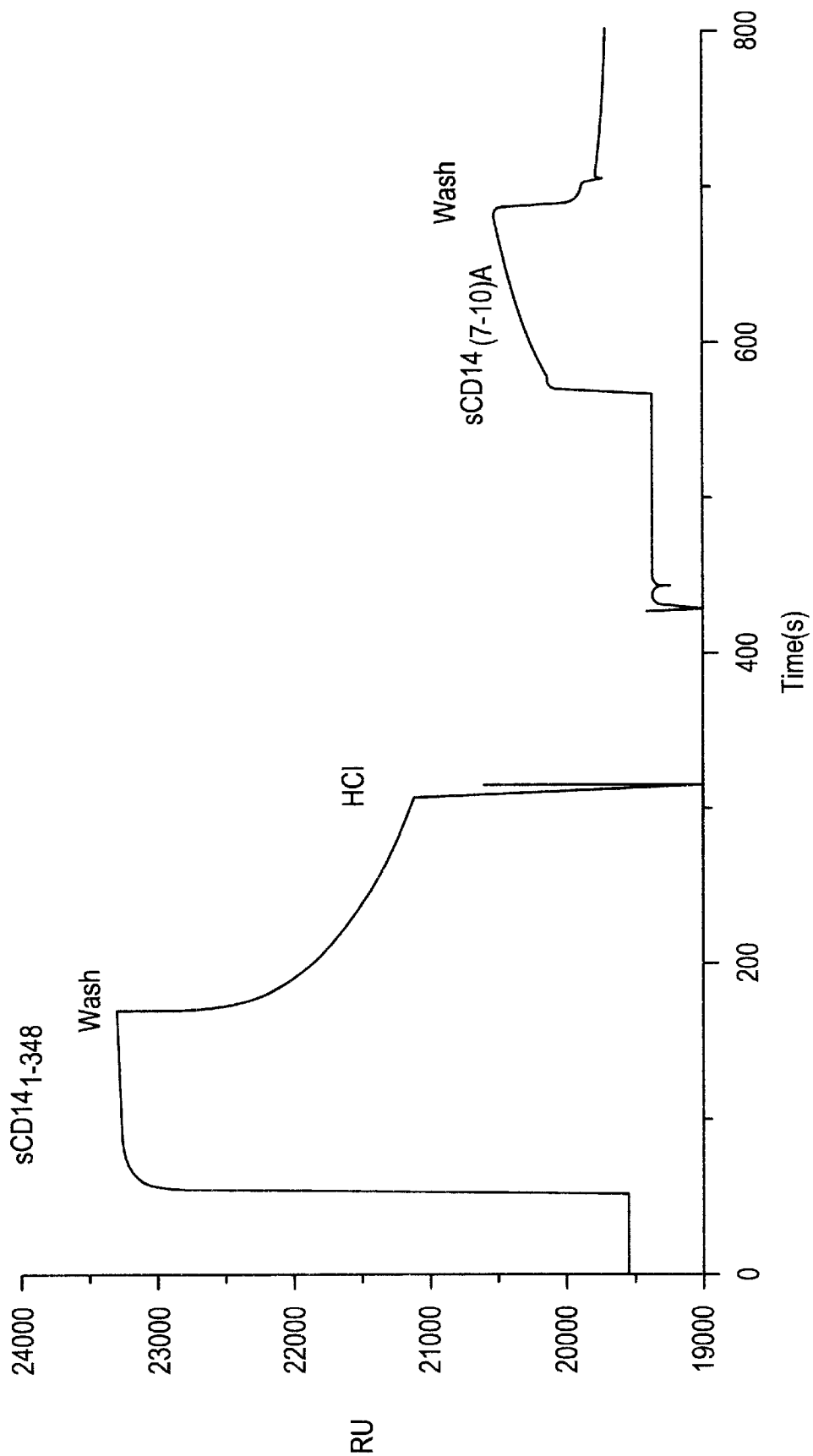
FIG. 4 shows that mAb 3C10 does not recognize purified sCD14$_{(7-10)A}$. Immobilization of mAb 3C10 to a sensor chip has been described (Juan, T. S. -C., et al. *J. Biol. Chem.* 270, 1382–1387 (1995)). 10 μg/ml sCD14$_{1-348}$ or sCD14$_{(7-10)A}$ was used for injection. Injection of solutions at various "Steps" are marked on the sensorgram. "Wash" indicates a washing step using HBS buffer as described in the Example Section. The experiments were performed three times and the results of one experiment are shown.

BIAcore realtime analysis was again used to determine whether mAb 3C10 is able to bind purified sCD14$_{(7-10)A}$. FIG. 4 shows that sCD14$_{1-348}$ recognized immobilized 3C10 and caused an increase of 1800 RU 2 min after wash (compare RU of the sensorgram before HCl injection at T=300 to that before injection of sCD14$_{1-348}$ at T=0), confirming previous observations (Juan, T. S. -C., et al. *J. Biol. Chem.* 270, 1382–1387 (1995)). However, purified sCD14$_{(7-10)A}$ failed to recognize 3C10 and caused only slight RU change (compare RU of the sensorgram after second wash at T=750 to that before injection of sCD14$_{1-348}$ at T=0) similar to that observed when an irrelevant protein such as bovine serum albumin was injected (data not shown), demonstrating that amino acids 7–10 are required for mAb 3C10 binding.

Example 4
sCD14$_{(7-10)A}$ has Reduced Ability to Mediate Cellular Responses to LPS.

To assess the consequences of mutating residues between 7 and 10 in sCD14, we used two previously described assays (Hailman, E., et al. *J. Exp. Med.* 179, 269–277 (1994); Juan, T. S. -C., et al. *J. Biol. Chem.* 270, 1382–1387 (1995); Frey, E. A., et al. *J. Exp. Med.* 176, 1665–1671 (1992)) to measure sCD14$_{(7-10)A}$ bioactivity. We first examined the ability of sCD14$_{(7-10)A}$ to enable responses of U373 cells to LPS. Addition of as little as 5 ng/ml sCD14$_{1-348}$ in the presence of LPS enabled strong IL-6 production (FIG. 5A). In contrast, sCD14$_{(7-10)A}$ was greatly impaired in its ability to enable responses, and required approximately 10-fold more protein in order to give a similar response to that of sCD14$_{1-348}$ (FIG. 5A).

Figure 5B:
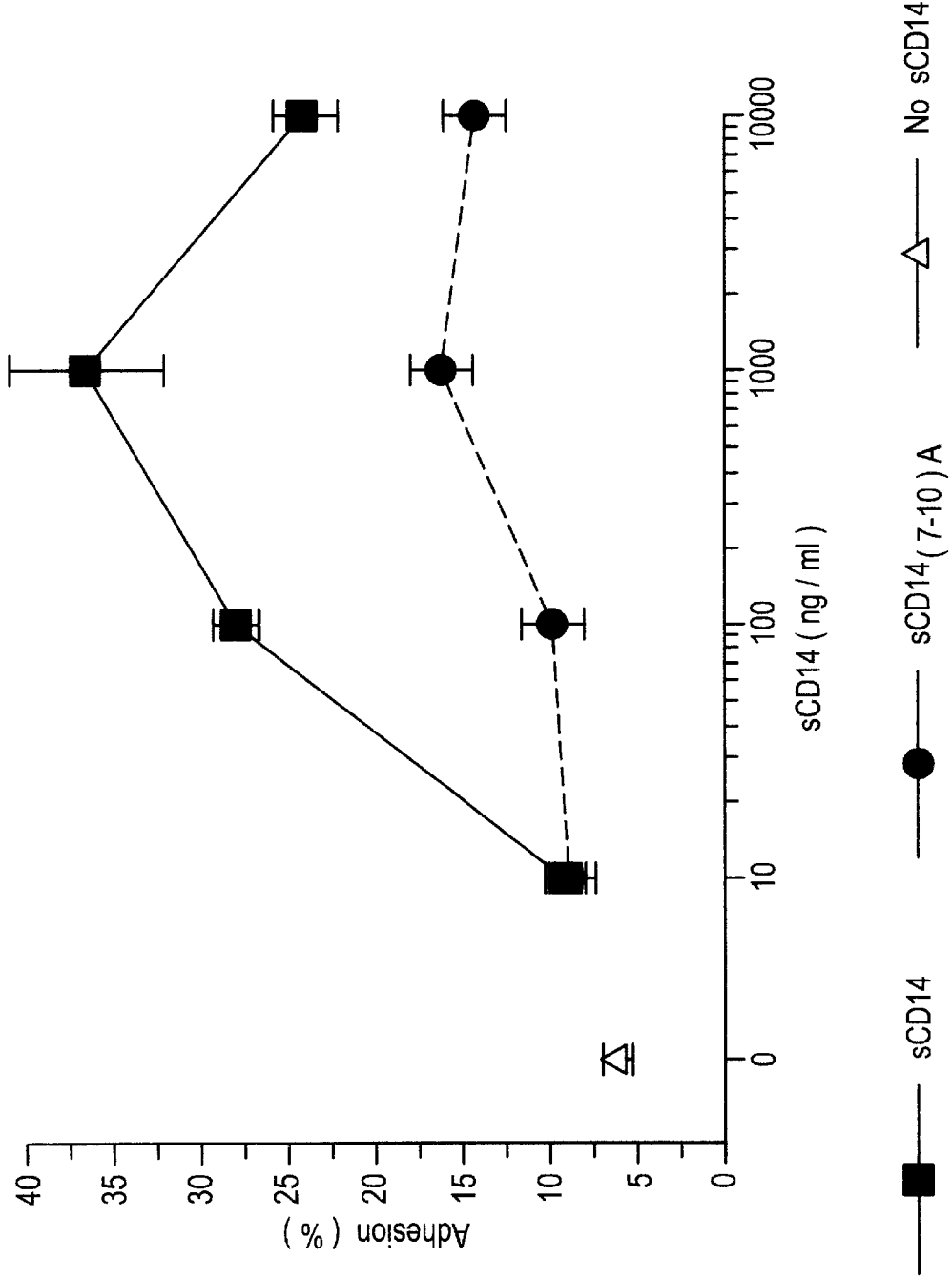
FIG. 5B. sCD14$_{1-348}$ but not sCD14$_{(7-10)A}$ mediates responses of PMN to LPS and LBP. Freshly isolated PMN were incubated with "smooth" LPS (*E. coli* 0111:B4 30 ng/ml), rLBP (1 μg/ml), and the indicated concentrations of sCD14$_{1-348}$ or sCD14$_{(7-10)A}$ for 10 min at 37° C. Cells were washed and adhesion to fibrinogen-coated wells was measured (Hailman, E., et al. J. Exp. Med. 179, 269–277 (1994),25). Error bars indicate standard deviations of triplicate determinations.

We also examined whether sCD14$_{(7-10)A}$ could enable LPS-induced adhesion of PMN to fibrinogen. FIG. 5B shows that 100 ng/ml sCD14$_{1-348}$ enabled a strong adhesive response of PMN to smooth LPS and rLBP. However, very little response was seen even when 10,000 ng/ml sCD14$_{(7-10)A}$ was added. These findings confirm that the region between amino acids 7 and 10 are necessary for the biological activity of sCD14.

Example 5
sCD14$_{(7-10)A}$ is Impaired in its Ability to Activate Transcription Factor NF-κB in the Presence of LPS.

Figure 6:
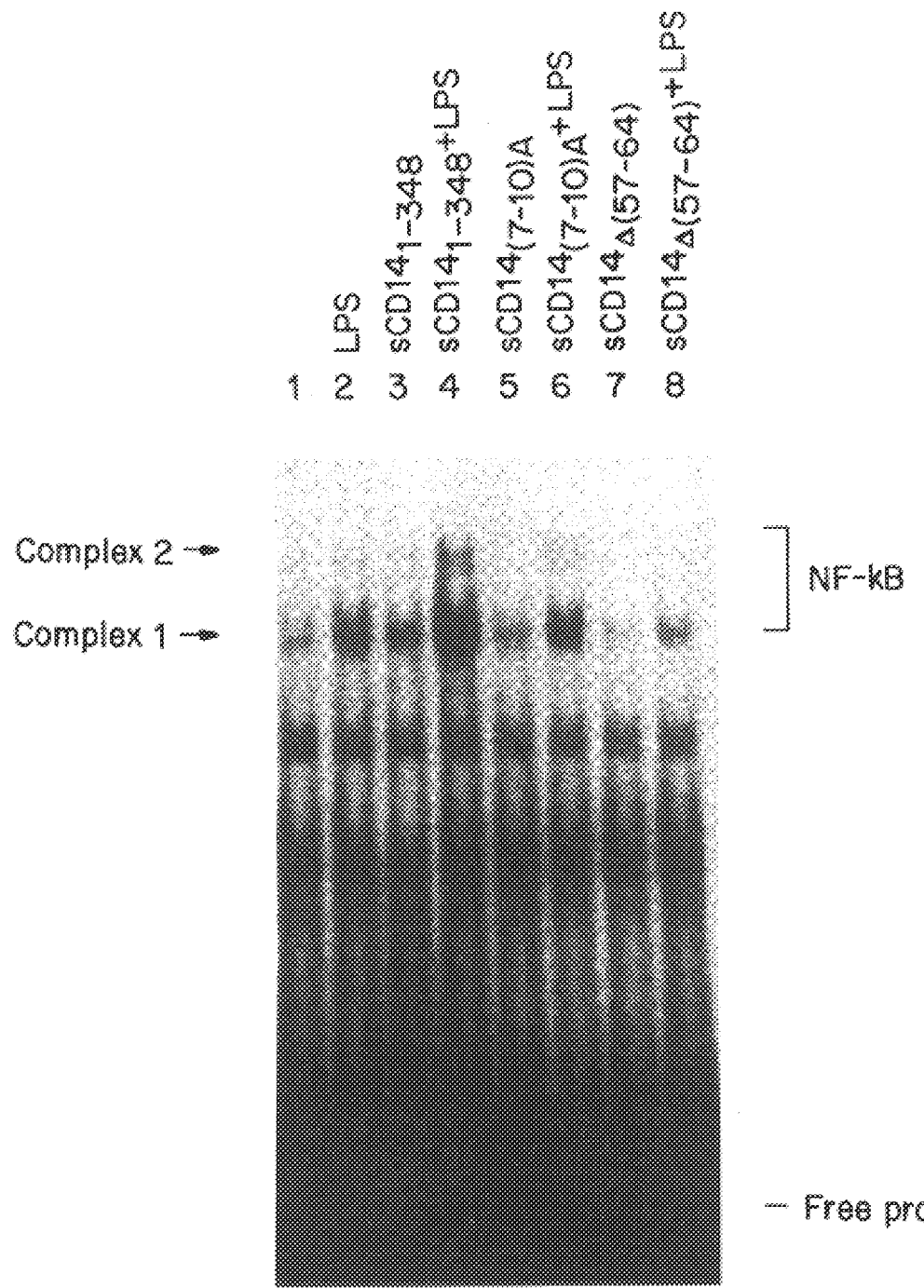
FIG. 6 shows that sCD14$_{(7-10)A}$ does not activate NF-κB. Whole cell extracts of U373 cells with various treatments (lane 1, control; lane 2, LPS; lane 3, sCD14$_{1-348}$; lane 4, sCD14$_{1-348}$ and LPS; lane 5, sCD14$_{(7-10)A}$; lane 6, sCD14$_{(7-10)A}$ and LPS; lane 7, sCD14$_{A(57-64)}$; and lane 8, sCD14$_{A(57-64)}$ and LPS) were obtained and binding of proteins to the labeled NF-κB oligonucleotide was performed as described in the Example Section. Complexes of NF-κB were resolved on a native-4.5% polyacrylamide gel. After electrophoresis, the gel was dried and exposed to X-ray film for 16 h. Complexes of labeled probe and NF-κB are indicated.

LPS and sCD14-mediated activation of cells has been shown to involve activation of transcription factors such as NF-κB (Sen, R., and Baltimore, D. *Cell* 47, 921–928 (1986); Lee, J. D., et al. *J. Exp. Med.* 175, 1697–1705 (1992); Bagasra, D., et al. *Proc. Natl. Acad. Sci. U. S. A.* 89, 6285–6289 (1992)). To assess whether the mutation in sCD14$_{(7-10)A}$ affected downstream signaling, we examined NF-κB activation in U373 cells treated with wildtype or mutant sCD14. In the absence of LPS or sCD14, U373 cells possess endogenous NF-κB which forms a complex with labeled NF-κB probe (Complex 1, FIG. 6, lane 1). Stimulation with LPS alone or sCD14$_{1-348}$ alone caused slight enhancement of NF-κB complex 1 and slight induction of a new NF-κB complex (Complex 2, FIG. 6, lanes 2 and 3), but addition of sCD14$_{1-348}$ and LPS greatly induced both complexes of NF-κB (FIG. 6, compare lanes 1 and 4). Both complexes 1 and 2 are NF-κB specific since a 100-fold excess of unlabelled NF-κB oligonucleotide pre-incubated with extracts of U373 cells eliminated formation of both complexes (data not shown). Stimulation of U373 cells with sCD14$_{(7-10)A}$ and LPS caused only 5% of NF-kB activation as quantitated by gel scanning (FIG. 6, lane 6). Comparatively, stimulation of U373 cells with a mutant which does not bind LPS (sCD14$_{\Delta57-64}$) [Note: Δ57–64 means deletion of amino acids 57–64] failed to activate NF-κB complexes even in the presence of LPS (FIG. 6, lane 8). These data indicate that a defect in sCD14$_{(7-10)A}$ is observed at the level at the transcription factor NF-κB. Since activation of NF-κB is an early event in signal transduction (Grilli, M., et al. *Int. Rev. Cytol.* 143, 1–62 (1993)), these data suggest that sCD14$_{(7-10)A}$ fails to enable signaling.

Example 6
sCD14$_{(7-10)A}$ Forms A Stable Complex with LPS.

Figure 7A:
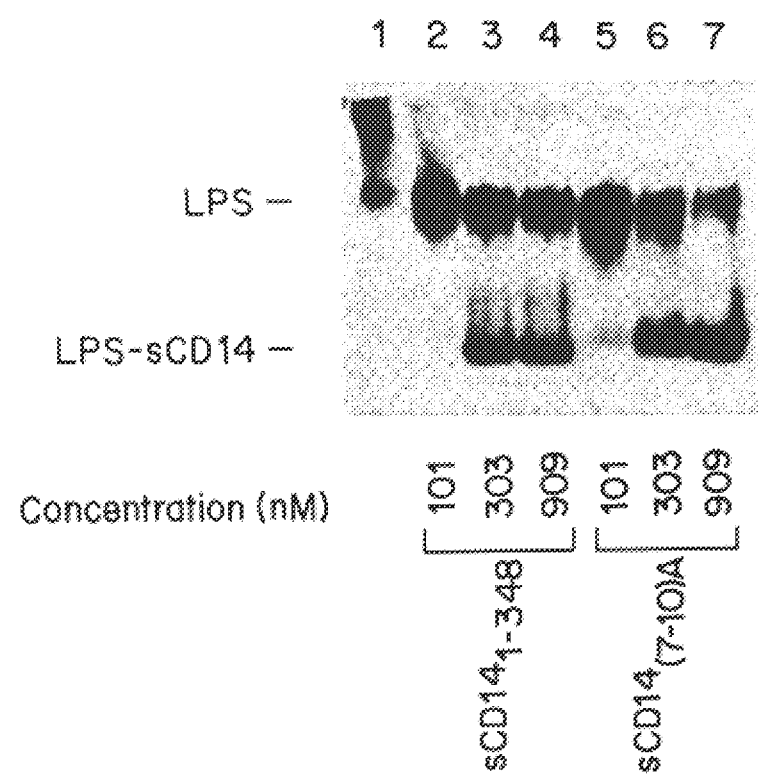
FIGS. 7A and B shows that sCD14$_{(7-10)A}$ forms stable complexes with $^3$H-LPS. Various concentrations of sCD14$_{1-348}$ (lanes 2–4) or sCD14$_{(7-10)A}$ (lanes 5–7) were incubated with 3 μg/ml $^3$H-LPS in the absence (7A) or presence of 16.7 nM rLBP (7B) as described in the Example Section. Lane 1 contains LPS in the absence of additional protein. Mixtures were run on 4–20% native polyacrylamide gels and processed for fluorography. Positions of uncomplexed LPS and complexes between LPS and sCD14$_{1-348}$ or sCD14$_{(7-10)A}$ are indicated.

Reduced signaling by sCD14$_{(7-10)A}$ could be due to a defect in binding LPS. To directly assess whether sCD14$_{(7-10)A}$ binds LPS normally, we used a native PAGE assay to detect stable complexes between sCD14$_{1-348}$ or sCD14$_{(7-10)A}$ and $^3$H-LPS. As previously reported (Hailman, E., et al. *J. Exp. Med.* 179, 269–277 (1994)), formation of stable complexes between sCD14$_{1-348}$ and LPS could be observed after 30 min of incubation (FIG. 7A), and addition of rLBP lowered the concentration of sCD14$_{1-348}$ required for complex formation (compare lane 2 of FIG. 7B to lane 2 of FIG. 7A). This is consistent with the previous observation (Hailman, E., et al. *J. Exp. Med.* 179, 269–277 (1994)) that rLBP accelerates the transfer of LPS to sCD14. Interestingly, sCD14$_{(7-10)A}$ was also able to form stable complexes with $^3$H-LPS in the absence of rLBP (FIG. 7A, lanes 5–7), and this complex formation was also facilitated by rLBP (compare lane 5 of FIG. 7B to lane 5 of FIG. 7A). These data confirm that sCD14$_{(7-10)A}$ is capable of binding LPS in an LBP-facilitated and in an LBP-independent fashion in vitro and suggest that the reduced biological activity of sCD14$_{(7-10)A}$ is not due to an inability to bind LPS.

Example 7
Inhibition of LPS-induced Cellular Responses by High Concentrations of sCD14.

Figure 8B:
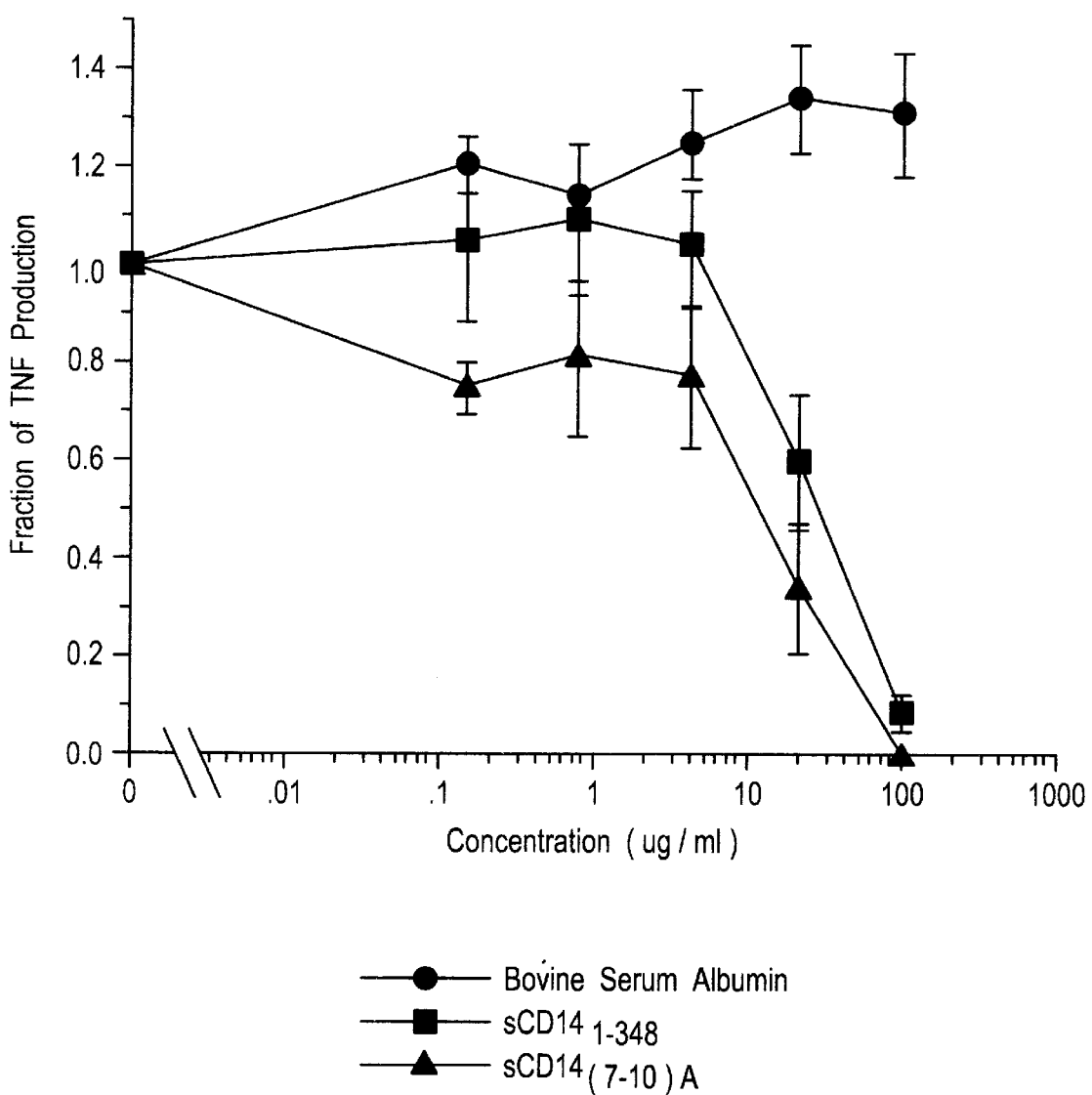
FIGS. 8A and B shows inhibition of LPS-induced cellular responses by sCD14$_{(7-10)A}$. 8A. Inhibition of LPS-induced PMN adhesion by sCD14$_{(7-10)A}$. Rough LPS (*Salmonella minnesota* R60, 10 ng/ml) was incubated with LBP and various concentrations of sCD14$_{1-348}$ or sCD14$_{(7-10)A}$ at 37° C. for 30 min before addition of PMN. The adhesion of PMN to fibrinogen was measured as described in the Example Section. Error bars indicate standard deviations from three readings. 8B. Inhibition of TNF-α production in whole blood by sCD14$_{(7-10)A}$. 250 μl of whole blood was incubated with various concentrations of bovine serum albumin, sCD14$_{1-348}$, or sCD14$_{(7-10)A}$ in the presence of 0.25 ng/ml smooth LPS (*Salmonella minnesota* wildtype) at 37° C. for 3 h and TNF-α production was measured as described in the Example Section. Fraction of TNF-α production refers to the ratio of TNF-α produced in the presence of exogenous protein divided by TNF-α produced in the absence of added protein. Error bars are standard deviations from six readings.

To further confirm that sCD14$_{(7-10)A}$ could bind LPS, we utilized two cell-based assays in which high concentrations of sCD14 prevent LPS-mediated activation of cells. In the first assay, sCD14$_{1-348}$ or sCD14$_{(7-10)A}$ were tested for their ability to inhibit adhesion of PMN to fibrinogen induced by LPS (FIG. 8A). In this experiment, constant concentrations of LPS and rLBP were incubated with increasing amounts (from 1 to 100 μg/ml) of sCD14$_{1-348}$ or sCD14$_{(7-10)A}$. Both proteins were capable of neutralizing LPS and inhibiting the adhesion of PMN induced by LPS.

We also examined whether sCD14$_{(7-10)A}$ could inhibit LPS-mediated TNF-α production in a whole blood assay, as has been shown for a recombinant sCD14 expressed in Baculovirus (Haziot, A., et al. *J. Immunol* 152, 5868–5876 (1994)). Addition of increasing amounts of sCD14$_{1-348}$ or sCD14$_{(7-10)A}$ caused inhibition of TNF-α production in the whole blood assay (FIG. 8B), while addition of bovine serum albumin did not inhibit TNF-α production, confirming the previous observation (Haziot, A., et al. *J. Immunol* 152, 5868–5876 (1994)). These data confirm that sCD14$_{(7-10)A}$ interacts with LPS as well as sCD14$_{1-348}$.

Discussion of Examples 1–7

In the above examples, we mapped the epitope for neutralizing mAb 3C10 to the region between amino acids 7 and 14 of sCD14. Substitution of alanine residues in this region prevented binding of 3C10 to sCD14. These data are consistent with our previous finding (Juan, T. S. -C., et al. *J. Biol. Chem.* 270, 1382–1387 (1995); Juan, T. S. -C., et al. *J. Biol. Chem.* 270, 5219–5224 (1995)) that the 3C10 epitope is located within the first 152 amino acids of sCD14 and is distinct from the epitope of MEM-18 at residues 57–64. To help understand how the 3C10 epitope contributes to CD14 function, we purified sCD14$_{(7-10)A}$ and showed that this protein was severely impaired in its ability to activate cells. Inability of this protein to promote activation of NF-κB suggests that sCD14$_{(7-10)A}$ fails to support LPS-mediated signaling.

Figure 7B:
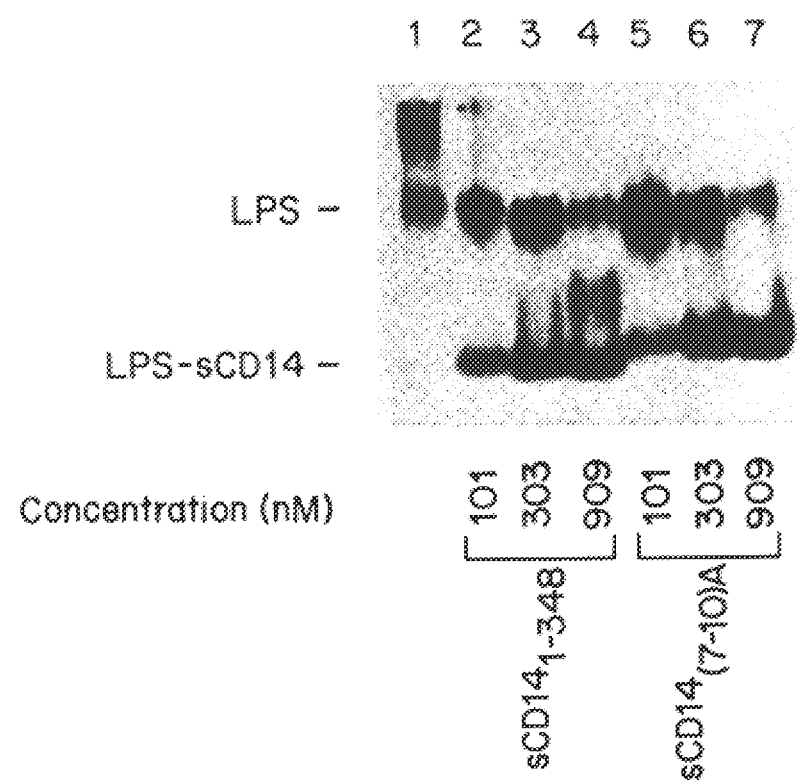

The defect in sCD14$_{(7-10)A}$ signaling is unlikely to result from an inability of this protein to bind LPS properly or to interact with LBP. sCD14$_{(7-10)A}$ binds LPS normally, as examined by gelshift (FIG. 7A) and two cell-based assays (FIG. 8) and rLBP facilitates transfer of LPS to sCD14$_{(7-10)A}$ (FIG. 7B). These data confirm our previous observation that 3C10 binds normally to complexes of sCD14 and LPS (Juan, T. S. -C., et al. *J. Biol. Chem.* 270, 5219–5224 (1995)). These experiments measured direct binding of LPS to sCD14$_{(7-10)A}$, not the binding of LPS-LBP complexes to cell surface CD14 measured in other reports (Wright, S. D., et al. *Science* 249: 1431–1433 (1990); Viriyakosol, S. and Kirkland, T. N. *J. Biol. Chem.* 270, 361–368 (1995).

Since sCD14$_{(7-10)A}$ binds LPS normally, its defect in signaling is likely to be manifest at the cell membrane. We (Frey, E. A., et al. *J. Exp. Med.* 176, 1665–1671 (1992)) and others (Pugin, J., et al. *Proc. Natl. Acad. Sci. U. S. A.* 90, 2744–2748 (1993); Haziot, A., et al. *J. Immunol* 151, 1500–1507 (1993); Arditi, M., et al. *Infect. Immun.* 61, 3149–3156 (1993)) have postulated the existence of a transmembrane protein that interacts with LPS and/or CD14 and transmits signals to the cytoplasm. It is thus possible that residues 7–10 are essential for the interaction of sCD14 with this transmembrane constituent. Alternatively, sCD14$_{(7-10)A}$ may be defective in delivering LPS to the lipid bilayer of cells. We have recently shown sCD14 rapidly shuttles LPS into HDL particles (Wurfel, M. M., et al. *J. Exp. Med.* J. Exp. Med. 181: 1743–1754 (1995)) and into phospholipid vesicles (M. M. Wurfel and S. D. W., manuscript in preparation), and it is thus possible that residues 7–10 are essential for delivery of bound LPS into the plasma membrane of cells.

Example 8

Gram Positive Cell Components Compete with LPS for Binding to sCD14

Figure 9:
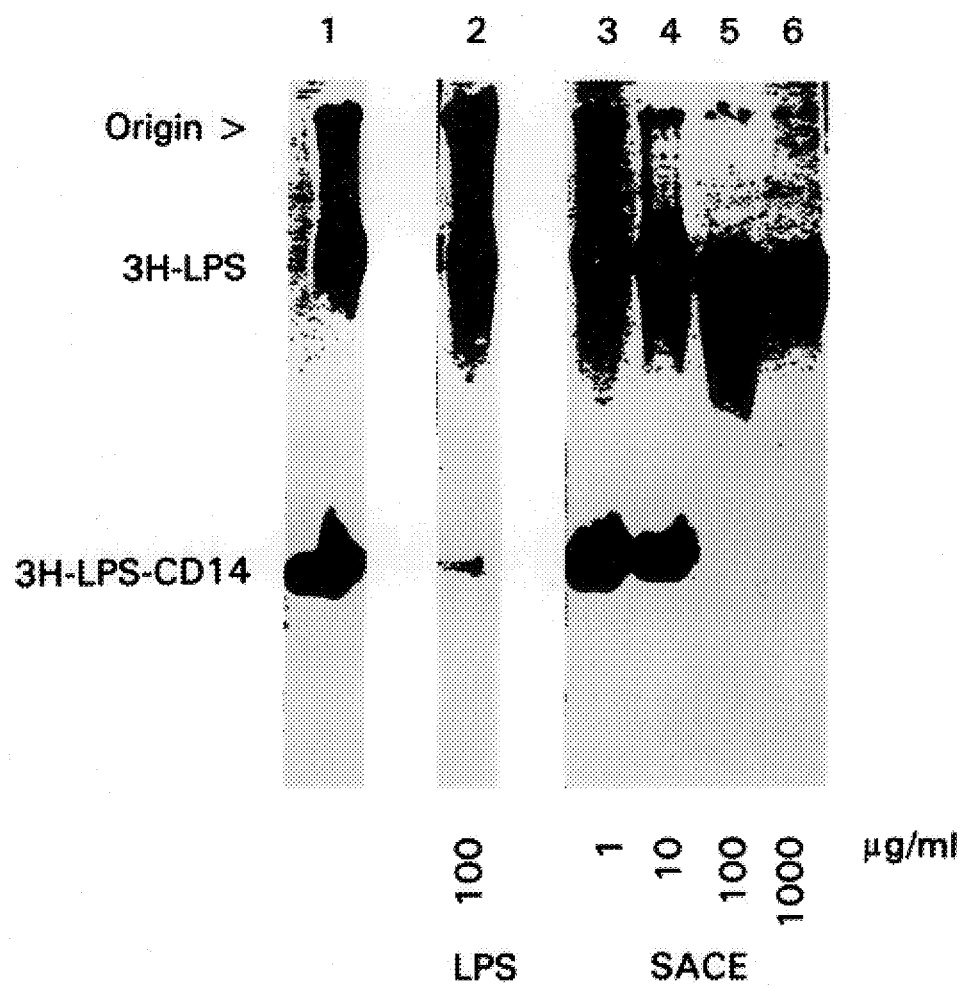
FIG. 9 shows that gram positive cell components compete with LPS for binding to sCD14. $^3$H-LPS (1 μg/ml) and sCD14 (50 μg/ml) were incubated alone (lane 1) or with LPS (lane 2) or with Staphylococcus aureus crude extract (SACE) (lanes 3–6) at 37° C. for 17 hours in PBS with 1 mM EDTA. The samples were then run in a native polyacrylamide gel, and the position of radioactive bands was determined by radioautography.

FIG. 9 presents the evidence that a gram-positive molecule present in the phenol extract of *S. aureus* (SACE) can bind to sCD14 and compete with LPS for a binding site. Other data (not shown) indicates that SACE strongly stimulates cells in a CD14-dependent fashion. The binding site(s) now defined on CD14 may be relevant not only to responses initiated by gram-negative but also by gram-positive bacteria.

Abbreviations

The abbreviations used in the Examples section above are: BCIP, 5-bromo-4-chloro-3-indoyl phosphate-toluidine salt; BPI, bactericidal/permeability-increasing protein; CHO, Chinese hamster ovary; CD, circular dichroism; CM, conditioned medium; HBSS, Hank's balanced salt solution; IL-6, interleukin-6; LALF, Limulus anti-LPS factor; LBP, LPS-binding protein; LPS, lipopolysaccharide; NBT, p-nitro blue tetrazolium chloride; PAGE, polyacrylamide gel electrophoresis; PBS, phosphate-buffered saline; PMN, polymorphonuclear leukocyte; r, recombinant; RU, response unit; sCD14, soluble CD14; ELISA, enzyme linked immunosorbant assay.

The invention now being fully described, it will be apparent to one of ordinary skill in the art that many changes and modifications can be made thereto, without departing from the spirit and scope of the invention as set forth herein.

The embodiments of the invention in which an exclusive property or privilege is claimed are defined as follows:

1. A polypeptide comprising an amino acid sequence that begins with one of amino acids 1 through 6 and ends with one of amino acids 152 through 348 of SEQ ID NO:38, wherein Xaa Xaa Xaa Xaa are each independently selected from the group consisting of Gly, Ala, Val, Leu, Ile and Pro; and physiologically acceptable salts thereof wherein said polypeptide is soluble, binds to LPS and mediates a substantially reduced cellular inflammatory response compared to native CD14.

2. A polypeptide according to claim 1, wherein said amino acid sequence comprises amino acids 1–152.

3. A polypeptide according to claim 1, wherein said amino acid sequence comprises amino acids 1–348.

4. A polypeptide according to claim 1, wherein Xaa Xaa Xaa Xaa are each Ala.

5. A polypeptide according to claim 1, wherein Xaa Xaa Xaa Xaa are each amino acids of the L configuration.

6. A polypeptide according to claim 1, wherein said sequence comprises amino acids 1–152 or 1–348 of SEQ ID NO.38 and wherein Xaa Xaa Xaa Xaa are each L-Ala.

7. A polypeptide consisting of a fragment of SEQ ID NO. 38 that contains a deletion of at least one of redsidues 7–14 and ends with one of amino acids 152 through 348 of the sequence of SEQ ID NO:38, and physiologically acceptable salts thereof wherein said polypeptide is soluble, binds to LPS and mediates a substantially reduced cellular inflammatory response compared to native CD14.

8. A polypeptide according to claim 7, wherein said amino acid sequence consists essentially of amino acids 15–152 SEQ ID NO.38.

9. A polypeptide according to claim 7, wherein said amino acid sequence consists essentially of amino acids 15–348 SEQ ID NO.38.

10. A polynucleotide that encodes a polypeptide according to claim 1 or claim 7.

11. A polynucleotide according to claim 10 which is DNA.

12. A method of reducing the severity of mediated inflammatory condition in a patient in need thereof, which comprises administering to said patient an effective amount of a polypeptide according to claim 1 or claim 7 thereby inhibiting the binding of CD14 cell surface antigen to lipopolysaccharide.

13. A method according to claim 12 wherein said amount is from 0.1 mg/kg to 100 mg/kg.

14. A pharmaceutical composition comprising a polypeptide according to claim 1 or claim 7 in admixture with a pharmaceutically acceptable carrier thereof.

* * * * *

UNITED STATES PATENT AND TRADEMARK OFFICE
CERTIFICATE OF CORRECTION

PATENT NO. : 5,869,055
DATED : February 9, 1999
INVENTOR(S) : Juan et al.

It is certified that error appears in the above-identified patent and that said Letters Patent is hereby corrected as shown below:

Column 5, line 20: After "FIG. 5" insert --A--.

Column 56, line 1: Just before "mediated" insert --lipopolysaccharide--.

Signed and Sealed this

Thirteenth Day of July, 1999

Attest:

Attesting Officer

Q. TODD DICKINSON
Acting Commissioner of Patents and Trademarks

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

Glu  Leu  Asp  Asp
1

( 2 ) INFORMATION FOR SEQ ID NO:2:

( i ) SEQUENCE CHARACTERISTICS:
( A ) LENGTH: 348 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

```
Thr Thr Pro Glu Pro Cys Gly Gly Gly Glu Asp Phe Arg Cys Val
 1               5                  10                  15

Cys Asn Phe Ser Glu Pro Gln Pro Asp Trp Ser Glu Ala Phe Gln Cys
            20              25                  30

Val Ser Ala Val Glu Val Glu Ile His Ala Gly Gly Leu Asn Leu Glu
         35              40                  45

Pro Phe Leu Lys Arg Val Asp Ala Asp Ala Asp Pro Arg Gln Tyr Ala
     50                  55                  60

Asp Thr Val Lys Ala Leu Arg Val Arg Arg Leu Thr Val Gly Ala Ala
 65                  70                  75                  80

Gln Val Pro Ala Gln Leu Leu Val Gly Ala Leu Arg Val Leu Ala Tyr
                 85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
            115                 120                 125

Arg Leu Arg Asn Val Ser Trp Ala Thr Gly Arg Ser Trp Leu Ala Glu
    130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
                180                 185                 190

Leu Met Ala Ala Leu Cys Pro His Lys Phe Pro Ala Ile Gln Asn Leu
        195                 200                 205

Ala Leu Arg Asn Thr Gly Met Glu Thr Pro Thr Gly Val Cys Ala Ala
    210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
            260                 265                 270

Pro Lys Gly Leu Pro Ala Lys Leu Arg Val Leu Asp Leu Ser Cys Asn
        275                 280                 285

Arg Leu Asn Arg Ala Pro Gln Pro Asp Glu Leu Pro Glu Val Asp Asn
    290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu
                340                 345
```

(2) INFORMATION FOR SEQ ID NO:3:

(i) SEQUENCE CHARACTERISTICS:
(A) LENGTH: 348 amino acids
(B) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:3:

| Thr | Thr | Pro | Glu | Pro | Cys | Ala | Ala | Ala | Ala | Glu | Asp | Phe | Arg | Cys | Val |
|---|---|---|---|---|---|---|---|---|---|---|---|---|---|---|---|
| 1 | | | | 5 | | | | | 10 | | | | | 15 | |
| Cys | Asn | Phe | Ser | Glu | Pro | Gln | Pro | Asp | Trp | Ser | Glu | Ala | Phe | Gln | Cys |
| | | | 20 | | | | | 25 | | | | | 30 | | |
| Val | Ser | Ala | Val | Glu | Val | Glu | Ile | His | Ala | Gly | Gly | Leu | Asn | Leu | Glu |
| | | 35 | | | | | 40 | | | | | 45 | | | |
| Pro | Phe | Leu | Lys | Arg | Val | Asp | Ala | Asp | Ala | Asp | Pro | Arg | Gln | Tyr | Ala |
| | | 50 | | | | | 55 | | | | 60 | | | | |
| Asp | Thr | Val | Lys | Ala | Leu | Arg | Val | Arg | Arg | Leu | Thr | Val | Gly | Ala | Ala |
| 65 | | | | | 70 | | | | | 75 | | | | | 80 |
| Gln | Val | Pro | Ala | Gln | Leu | Leu | Val | Gly | Ala | Leu | Arg | Val | Leu | Ala | Tyr |
| | | | | 85 | | | | | 90 | | | | | 95 | |
| Ser | Arg | Leu | Lys | Glu | Leu | Thr | Leu | Glu | Asp | Leu | Lys | Ile | Thr | Gly | Thr |
| | | | 100 | | | | | 105 | | | | | 110 | | |
| Met | Pro | Pro | Leu | Pro | Leu | Glu | Ala | Thr | Gly | Leu | Ala | Leu | Ser | Ser | Leu |
| | | 115 | | | | | 120 | | | | | 125 | | | |
| Arg | Leu | Arg | Asn | Val | Ser | Trp | Ala | Thr | Gly | Arg | Ser | Trp | Leu | Ala | Glu |
| | 130 | | | | | 135 | | | | | 140 | | | | |
| Leu | Gln | Gln | Trp | Leu | Lys | Pro | Gly | Leu | Lys | Val | Leu | Ser | Ile | Ala | Gln |
| 145 | | | | | 150 | | | | | 155 | | | | | 160 |
| Ala | His | Ser | Pro | Ala | Phe | Ser | Cys | Glu | Gln | Val | Arg | Ala | Phe | Pro | Ala |
| | | | | 165 | | | | | 170 | | | | | 175 | |
| Leu | Thr | Ser | Leu | Asp | Leu | Ser | Asp | Asn | Pro | Gly | Leu | Gly | Glu | Arg | Gly |
| | | | 180 | | | | | 185 | | | | | 190 | | |
| Leu | Met | Ala | Ala | Leu | Cys | Pro | His | Lys | Phe | Pro | Ala | Ile | Gln | Asn | Leu |
| | | 195 | | | | | 200 | | | | | 205 | | | |
| Ala | Leu | Arg | Asn | Thr | Gly | Met | Glu | Thr | Pro | Thr | Gly | Val | Cys | Ala | Ala |
| | 210 | | | | | 215 | | | | | 220 | | | | |
| Leu | Ala | Ala | Ala | Gly | Val | Gln | Pro | His | Ser | Leu | Asp | Leu | Ser | His | Asn |
| 225 | | | | | 230 | | | | | 235 | | | | | 240 |
| Ser | Leu | Arg | Ala | Thr | Val | Asn | Pro | Ser | Ala | Pro | Arg | Cys | Met | Trp | Ser |
| | | | | 245 | | | | | 250 | | | | | 255 | |
| Ser | Ala | Leu | Asn | Ser | Leu | Asn | Leu | Ser | Phe | Ala | Gly | Leu | Glu | Gln | Val |
| | | | 260 | | | | | 265 | | | | | 270 | | |
| Pro | Lys | Gly | Leu | Pro | Ala | Lys | Leu | Arg | Val | Leu | Asp | Leu | Ser | Cys | Asn |
| | | 275 | | | | | 280 | | | | | 285 | | | |
| Arg | Leu | Asn | Arg | Ala | Pro | Gln | Pro | Asp | Glu | Leu | Pro | Glu | Val | Asp | Asn |
| | 290 | | | | | 295 | | | | | 300 | | | | |
| Leu | Thr | Leu | Asp | Gly | Asn | Pro | Phe | Leu | Val | Pro | Gly | Thr | Ala | Leu | Pro |
| 305 | | | | | 310 | | | | | 315 | | | | | 320 |
| His | Glu | Gly | Ser | Met | Asn | Ser | Gly | Val | Val | Pro | Ala | Cys | Ala | Arg | Ser |
| | | | | 325 | | | | | 330 | | | | | 335 | |
| Thr | Leu | Ser | Val | Gly | Val | Ser | Gly | Thr | Leu | Val | Leu | | | | |
| | | | 340 | | | | | 345 | | | | | | | |

( 2 ) INFORMATION FOR SEQ ID NO:4:

( i ) SEQUENCE CHARACTERISTICS:
( A ) LENGTH: 348 amino acids
( B ) TYPE: amino acid
( C ) STRANDEDNESS: single (D) TOPOLOGY: linear (ii) MOLECULE TYPE: protein (xi) SEQUENCE DESCRIPTION: SEQ ID NO:4:

| Thr | Thr | Pro | Glu | Pro | Cys | Val | Val | Val | Glu | Asp | Phe | Arg | Cys | Val |
| 1 | | | | 5 | | | | | 10 | | | | | 15 |
| Cys | Asn | Phe | Ser | Glu | Pro | Gln | Pro | Asp | Trp | Ser | Glu | Ala | Phe | Gln | Cys |
| | | | 20 | | | | 25 | | | | | 30 | | |
| Val | Ser | Ala | Val | Glu | Val | Glu | Ile | His | Ala | Gly | Gly | Leu | Asn | Leu | Glu |
| | | 35 | | | | 40 | | | | | 45 | | | |
| Pro | Phe | Leu | Lys | Arg | Val | Asp | Ala | Asp | Ala | Asp | Pro | Arg | Gln | Tyr | Ala |
| | 50 | | | | 55 | | | | | 60 | | | | |
| Asp | Thr | Val | Lys | Ala | Leu | Arg | Val | Arg | Arg | Leu | Thr | Val | Gly | Ala | Ala |
| 65 | | | | 70 | | | | | 75 | | | | | 80 |
| Gln | Val | Pro | Ala | Gln | Leu | Leu | Val | Gly | Ala | Leu | Arg | Val | Leu | Ala | Tyr |
| | | | 85 | | | | 90 | | | | | 95 | | |
| Ser | Arg | Leu | Lys | Glu | Leu | Thr | Leu | Glu | Asp | Leu | Lys | Ile | Thr | Gly | Thr |
| | | | 100 | | | | 105 | | | | | 110 | | |
| Met | Pro | Pro | Leu | Pro | Leu | Glu | Ala | Thr | Gly | Leu | Ala | Leu | Ser | Ser | Leu |
| | | 115 | | | | 120 | | | | | 125 | | | |
| Arg | Leu | Arg | Asn | Val | Ser | Trp | Ala | Thr | Gly | Arg | Ser | Trp | Leu | Ala | Glu |
| | 130 | | | | 135 | | | | | 140 | | | | |
| Leu | Gln | Gln | Trp | Leu | Lys | Pro | Gly | Leu | Lys | Val | Leu | Ser | Ile | Ala | Gln |
| 145 | | | | 150 | | | | | 155 | | | | | 160 |
| Ala | His | Ser | Pro | Ala | Phe | Ser | Cys | Glu | Gln | Val | Arg | Ala | Phe | Pro | Ala |
| | | | 165 | | | | 170 | | | | | 175 | | |
| Leu | Thr | Ser | Leu | Asp | Leu | Ser | Asp | Asn | Pro | Gly | Leu | Gly | Glu | Arg | Gly |
| | | | 180 | | | | 185 | | | | | 190 | | |
| Leu | Met | Ala | Ala | Leu | Cys | Pro | His | Lys | Phe | Pro | Ala | Ile | Gln | Asn | Leu |
| | | 195 | | | | 200 | | | | | 205 | | | |
| Ala | Leu | Arg | Asn | Thr | Gly | Met | Glu | Thr | Pro | Thr | Gly | Val | Cys | Ala | Ala |
| | | 210 | | | | 215 | | | | | 220 | | | |
| Leu | Ala | Ala | Ala | Gly | Val | Gln | Pro | His | Ser | Leu | Asp | Leu | Ser | His | Asn |
| 225 | | | | 230 | | | | | 235 | | | | | 240 |
| Ser | Leu | Arg | Ala | Thr | Val | Asn | Pro | Ser | Ala | Pro | Arg | Cys | Met | Trp | Ser |
| | | | 245 | | | | 250 | | | | | 255 | | |
| Ser | Ala | Leu | Asn | Ser | Leu | Asn | Leu | Ser | Phe | Ala | Gly | Leu | Glu | Gln | Val |
| | | | 260 | | | | 265 | | | | | 270 | | |
| Pro | Lys | Gly | Leu | Pro | Ala | Lys | Leu | Arg | Val | Leu | Asp | Leu | Ser | Cys | Asn |
| | | 275 | | | | 280 | | | | | 285 | | | |
| Arg | Leu | Asn | Arg | Ala | Pro | Gln | Pro | Asp | Glu | Leu | Pro | Glu | Val | Asp | Asn |
| | 290 | | | | 295 | | | | | 300 | | | | |
| Leu | Thr | Leu | Asp | Gly | Asn | Pro | Phe | Leu | Val | Pro | Gly | Thr | Ala | Leu | Pro |
| 305 | | | | 310 | | | | | 315 | | | | | 320 |
| His | Glu | Gly | Ser | Met | Asn | Ser | Gly | Val | Val | Pro | Ala | Cys | Ala | Arg | Ser |
| | | | 325 | | | | 330 | | | | | 335 | | |
| Thr | Leu | Ser | Val | Gly | Val | Ser | Gly | Thr | Leu | Val | Leu |
| | | | 340 | | | | 345 | | | |

(2) INFORMATION FOR SEQ ID NO:5:

(i) SEQUENCE CHARACTERISTICS:
(A) LENGTH: 348 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:5:

| Thr | Thr | Pro | Glu | Pro | Cys | Leu | Leu | Leu | Glu | Asp | Phe | Arg | Cys | Val |
|---|---|---|---|---|---|---|---|---|---|---|---|---|---|---|
| 1 | | | | 5 | | | | | 10 | | | | | 15 |

| Cys | Asn | Phe | Ser | Glu | Pro | Gln | Pro | Asp | Trp | Ser | Glu | Ala | Phe | Gln | Cys |
|---|---|---|---|---|---|---|---|---|---|---|---|---|---|---|---|
| | | | 20 | | | | 25 | | | | | | 30 | | |

| Val | Ser | Ala | Val | Glu | Val | Glu | Ile | His | Ala | Gly | Gly | Leu | Asn | Leu | Glu |
|---|---|---|---|---|---|---|---|---|---|---|---|---|---|---|---|
| | | 35 | | | | | 40 | | | | | 45 | | | |

| Pro | Phe | Leu | Lys | Arg | Val | Asp | Ala | Asp | Ala | Asp | Pro | Arg | Gln | Tyr | Ala |
|---|---|---|---|---|---|---|---|---|---|---|---|---|---|---|---|
| | 50 | | | | | 55 | | | | | 60 | | | | |

| Asp | Thr | Val | Lys | Ala | Leu | Arg | Val | Arg | Arg | Leu | Thr | Val | Gly | Ala | Ala |
|---|---|---|---|---|---|---|---|---|---|---|---|---|---|---|---|
| 65 | | | | | 70 | | | | | 75 | | | | | 80 |

| Gln | Val | Pro | Ala | Gln | Leu | Leu | Val | Gly | Ala | Leu | Arg | Val | Leu | Ala | Tyr |
|---|---|---|---|---|---|---|---|---|---|---|---|---|---|---|---|
| | | | | 85 | | | | | 90 | | | | | 95 | |

| Ser | Arg | Leu | Lys | Glu | Leu | Thr | Leu | Glu | Asp | Leu | Lys | Ile | Thr | Gly | Thr |
|---|---|---|---|---|---|---|---|---|---|---|---|---|---|---|---|
| | | | | 100 | | | | | 105 | | | | 110 | | |

| Met | Pro | Pro | Leu | Pro | Leu | Glu | Ala | Thr | Gly | Leu | Ala | Leu | Ser | Ser | Leu |
|---|---|---|---|---|---|---|---|---|---|---|---|---|---|---|---|
| | | 115 | | | | | 120 | | | | | 125 | | | |

| Arg | Leu | Arg | Asn | Val | Ser | Trp | Ala | Thr | Gly | Arg | Ser | Trp | Leu | Ala | Glu |
|---|---|---|---|---|---|---|---|---|---|---|---|---|---|---|---|
| | 130 | | | | | 135 | | | | | 140 | | | | |

| Leu | Gln | Gln | Trp | Leu | Lys | Pro | Gly | Leu | Lys | Val | Leu | Ser | Ile | Ala | Gln |
|---|---|---|---|---|---|---|---|---|---|---|---|---|---|---|---|
| 145 | | | | | 150 | | | | | 155 | | | | | 160 |

| Ala | His | Ser | Pro | Ala | Phe | Ser | Cys | Glu | Gln | Val | Arg | Ala | Phe | Pro | Ala |
|---|---|---|---|---|---|---|---|---|---|---|---|---|---|---|---|
| | | | | 165 | | | | | 170 | | | | | 175 | |

| Leu | Thr | Ser | Leu | Asp | Leu | Ser | Asp | Asn | Pro | Gly | Leu | Gly | Glu | Arg | Gly |
|---|---|---|---|---|---|---|---|---|---|---|---|---|---|---|---|
| | | | 180 | | | | | 185 | | | | | 190 | | |

| Leu | Met | Ala | Ala | Leu | Cys | Pro | His | Lys | Phe | Pro | Ala | Ile | Gln | Asn | Leu |
|---|---|---|---|---|---|---|---|---|---|---|---|---|---|---|---|
| | | 195 | | | | | 200 | | | | | 205 | | | |

| Ala | Leu | Arg | Asn | Thr | Gly | Met | Glu | Thr | Pro | Thr | Gly | Val | Cys | Ala | Ala |
|---|---|---|---|---|---|---|---|---|---|---|---|---|---|---|---|
| | 210 | | | | | 215 | | | | | 220 | | | | |

| Leu | Ala | Ala | Ala | Gly | Val | Gln | Pro | His | Ser | Leu | Asp | Leu | Ser | His | Asn |
|---|---|---|---|---|---|---|---|---|---|---|---|---|---|---|---|
| 225 | | | | | 230 | | | | | 235 | | | | | 240 |

| Ser | Leu | Arg | Ala | Thr | Val | Asn | Pro | Ser | Ala | Pro | Arg | Cys | Met | Trp | Ser |
|---|---|---|---|---|---|---|---|---|---|---|---|---|---|---|---|
| | | | | 245 | | | | | 250 | | | | | 255 | |

| Ser | Ala | Leu | Asn | Ser | Leu | Asn | Leu | Ser | Phe | Ala | Gly | Leu | Glu | Gln | Val |
|---|---|---|---|---|---|---|---|---|---|---|---|---|---|---|---|
| | | | 260 | | | | | 265 | | | | | 270 | | |

| Pro | Lys | Gly | Leu | Pro | Ala | Lys | Leu | Arg | Val | Leu | Asp | Leu | Ser | Cys | Asn |
|---|---|---|---|---|---|---|---|---|---|---|---|---|---|---|---|
| | | 275 | | | | | 280 | | | | | 285 | | | |

| Arg | Leu | Asn | Arg | Ala | Pro | Gln | Pro | Asp | Glu | Leu | Pro | Glu | Val | Asp | Asn |
|---|---|---|---|---|---|---|---|---|---|---|---|---|---|---|---|
| | 290 | | | | | 295 | | | | | 300 | | | | |

| Leu | Thr | Leu | Asp | Gly | Asn | Pro | Phe | Leu | Val | Pro | Gly | Thr | Ala | Leu | Pro |
|---|---|---|---|---|---|---|---|---|---|---|---|---|---|---|---|
| 305 | | | | | 310 | | | | | 315 | | | | | 320 |

| His | Glu | Gly | Ser | Met | Asn | Ser | Gly | Val | Val | Pro | Ala | Cys | Ala | Arg | Ser |
|---|---|---|---|---|---|---|---|---|---|---|---|---|---|---|---|
| | | | | 325 | | | | | 330 | | | | | 335 | |

| Thr | Leu | Ser | Val | Gly | Val | Ser | Gly | Thr | Leu | Val | Leu |
|---|---|---|---|---|---|---|---|---|---|---|---|
| | | | 340 | | | | | 345 | | | |

(2) INFORMATION FOR SEQ ID NO:6:

(i) SEQUENCE CHARACTERISTICS:
    (A) LENGTH: 348 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:6:

| Thr | Thr | Pro | Glu | Pro | Cys | Ile | Ile | Ile | Ile | Glu | Asp | Phe | Arg | Cys | Val |
|---|---|---|---|---|---|---|---|---|---|---|---|---|---|---|---|
| 1 | | | | 5 | | | | | 10 | | | | | 15 | |
| Cys | Asn | Phe | Ser | Glu | Pro | Gln | Pro | Asp | Trp | Ser | Glu | Ala | Phe | Gln | Cys |
| | | | 20 | | | | 25 | | | | | 30 | | | |
| Val | Ser | Ala | Val | Glu | Val | Glu | Ile | His | Ala | Gly | Gly | Leu | Asn | Leu | Glu |
| | | 35 | | | | 40 | | | | | 45 | | | | |
| Pro | Phe | Leu | Lys | Arg | Val | Asp | Ala | Asp | Ala | Asp | Pro | Arg | Gln | Tyr | Ala |
| | 50 | | | | | 55 | | | | | 60 | | | | |
| Asp | Thr | Val | Lys | Ala | Leu | Arg | Val | Arg | Arg | Leu | Thr | Val | Gly | Ala | Ala |
| 65 | | | | | 70 | | | | | 75 | | | | | 80 |
| Gln | Val | Pro | Ala | Gln | Leu | Leu | Val | Gly | Ala | Leu | Arg | Val | Leu | Ala | Tyr |
| | | | | 85 | | | | | 90 | | | | | 95 | |
| Ser | Arg | Leu | Lys | Glu | Leu | Thr | Leu | Glu | Asp | Leu | Lys | Ile | Thr | Gly | Thr |
| | | | 100 | | | | | 105 | | | | | 110 | | |
| Met | Pro | Pro | Leu | Pro | Leu | Glu | Ala | Thr | Gly | Leu | Ala | Leu | Ser | Ser | Leu |
| | | 115 | | | | | 120 | | | | | 125 | | | |
| Arg | Leu | Arg | Asn | Val | Ser | Trp | Ala | Thr | Gly | Arg | Ser | Trp | Leu | Ala | Glu |
| | 130 | | | | | 135 | | | | | 140 | | | | |
| Leu | Gln | Gln | Trp | Leu | Lys | Pro | Gly | Leu | Lys | Val | Leu | Ser | Ile | Ala | Gln |
| 145 | | | | | 150 | | | | | 155 | | | | | 160 |
| Ala | His | Ser | Pro | Ala | Phe | Ser | Cys | Glu | Gln | Val | Arg | Ala | Phe | Pro | Ala |
| | | | | 165 | | | | | 170 | | | | | 175 | |
| Leu | Thr | Ser | Leu | Asp | Leu | Ser | Asp | Asn | Pro | Gly | Leu | Gly | Glu | Arg | Gly |
| | | | 180 | | | | | 185 | | | | | 190 | | |
| Leu | Met | Ala | Ala | Leu | Cys | Pro | His | Lys | Phe | Pro | Ala | Ile | Gln | Asn | Leu |
| | | 195 | | | | | 200 | | | | | 205 | | | |
| Ala | Leu | Arg | Asn | Thr | Gly | Met | Glu | Thr | Pro | Thr | Gly | Val | Cys | Ala | Ala |
| | 210 | | | | | 215 | | | | | 220 | | | | |
| Leu | Ala | Ala | Ala | Gly | Val | Gln | Pro | His | Ser | Leu | Asp | Leu | Ser | His | Asn |
| 225 | | | | | 230 | | | | | 235 | | | | | 240 |
| Ser | Leu | Arg | Ala | Thr | Val | Asn | Pro | Ser | Ala | Pro | Arg | Cys | Met | Trp | Ser |
| | | | | 245 | | | | | 250 | | | | | 255 | |
| Ser | Ala | Leu | Asn | Ser | Leu | Asn | Leu | Ser | Phe | Ala | Gly | Leu | Glu | Gln | Val |
| | | | 260 | | | | | 265 | | | | | 270 | | |
| Pro | Lys | Gly | Leu | Pro | Ala | Lys | Leu | Arg | Val | Leu | Asp | Leu | Ser | Cys | Asn |
| | | 275 | | | | | 280 | | | | | 285 | | | |
| Arg | Leu | Asn | Arg | Ala | Pro | Gln | Pro | Asp | Glu | Leu | Pro | Glu | Val | Asp | Asn |
| | 290 | | | | | 295 | | | | | 300 | | | | |
| Leu | Thr | Leu | Asp | Gly | Asn | Pro | Phe | Leu | Val | Pro | Gly | Thr | Ala | Leu | Pro |
| 305 | | | | | 310 | | | | | 315 | | | | | 320 |
| His | Glu | Gly | Ser | Met | Asn | Ser | Gly | Val | Val | Pro | Ala | Cys | Ala | Arg | Ser |
| | | | | 325 | | | | | 330 | | | | | 335 | |
| Thr | Leu | Ser | Val | Gly | Val | Ser | Gly | Thr | Leu | Val | Leu | | | | |
| | | | 340 | | | | | 345 | | | | | | | |

(2) INFORMATION FOR SEQ ID NO:7:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: protein ( x i ) SEQUENCE DESCRIPTION: SEQ ID NO:7:

| Thr | Thr | Pro | Glu | Pro | Cys | Pro | Pro | Pro | Glu | Asp | Phe | Arg | Cys | Val |
|---|---|---|---|---|---|---|---|---|---|---|---|---|---|---|
| 1 | | | | 5 | | | | | 10 | | | | | 15 |

| Cys | Asn | Phe | Ser | Glu | Pro | Gln | Pro | Asp | Trp | Ser | Glu | Ala | Phe | Gln | Cys |
|---|---|---|---|---|---|---|---|---|---|---|---|---|---|---|---|
| | | | 20 | | | | 25 | | | | | | 30 | | |

| Val | Ser | Ala | Val | Glu | Val | Glu | Ile | His | Ala | Gly | Gly | Leu | Asn | Leu | Glu |
|---|---|---|---|---|---|---|---|---|---|---|---|---|---|---|---|
| | | 35 | | | | | 40 | | | | | 45 | | | |

| Pro | Phe | Leu | Lys | Arg | Val | Asp | Ala | Asp | Ala | Asp | Pro | Arg | Gln | Tyr | Ala |
|---|---|---|---|---|---|---|---|---|---|---|---|---|---|---|---|
| | 50 | | | | | 55 | | | | | 60 | | | | |

| Asp | Thr | Val | Lys | Ala | Leu | Arg | Val | Arg | Arg | Leu | Thr | Val | Gly | Ala | Ala |
|---|---|---|---|---|---|---|---|---|---|---|---|---|---|---|---|
| 65 | | | | | 70 | | | | | 75 | | | | | 80 |

| Gln | Val | Pro | Ala | Gln | Leu | Leu | Val | Gly | Ala | Leu | Arg | Val | Leu | Ala | Tyr |
|---|---|---|---|---|---|---|---|---|---|---|---|---|---|---|---|
| | | | | 85 | | | | | 90 | | | | | 95 | |

| Ser | Arg | Leu | Lys | Glu | Leu | Thr | Leu | Glu | Asp | Leu | Lys | Ile | Thr | Gly | Thr |
|---|---|---|---|---|---|---|---|---|---|---|---|---|---|---|---|
| | | | 100 | | | | | 105 | | | | | 110 | | |

| Met | Pro | Pro | Leu | Pro | Leu | Glu | Ala | Thr | Gly | Leu | Ala | Leu | Ser | Ser | Leu |
|---|---|---|---|---|---|---|---|---|---|---|---|---|---|---|---|
| | | 115 | | | | | 120 | | | | | 125 | | | |

| Arg | Leu | Arg | Asn | Val | Ser | Trp | Ala | Thr | Gly | Arg | Ser | Trp | Leu | Ala | Glu |
|---|---|---|---|---|---|---|---|---|---|---|---|---|---|---|---|
| | 130 | | | | | 135 | | | | | 140 | | | | |

| Leu | Gln | Gln | Trp | Leu | Lys | Pro | Gly | Leu | Lys | Val | Leu | Ser | Ile | Ala | Gln |
|---|---|---|---|---|---|---|---|---|---|---|---|---|---|---|---|
| 145 | | | | | 150 | | | | | 155 | | | | | 160 |

| Ala | His | Ser | Pro | Ala | Phe | Ser | Cys | Glu | Gln | Val | Arg | Ala | Phe | Pro | Ala |
|---|---|---|---|---|---|---|---|---|---|---|---|---|---|---|---|
| | | | | 165 | | | | | 170 | | | | | 175 | |

| Leu | Thr | Ser | Leu | Asp | Leu | Ser | Asp | Asn | Pro | Gly | Leu | Gly | Glu | Arg | Gly |
|---|---|---|---|---|---|---|---|---|---|---|---|---|---|---|---|
| | | | 180 | | | | | 185 | | | | | 190 | | |

| Leu | Met | Ala | Ala | Leu | Cys | Pro | His | Lys | Phe | Pro | Ala | Ile | Gln | Asn | Leu |
|---|---|---|---|---|---|---|---|---|---|---|---|---|---|---|---|
| | | 195 | | | | | 200 | | | | | 205 | | | |

| Ala | Leu | Arg | Asn | Thr | Gly | Met | Glu | Thr | Pro | Thr | Gly | Val | Cys | Ala | Ala |
|---|---|---|---|---|---|---|---|---|---|---|---|---|---|---|---|
| | 210 | | | | | 215 | | | | | 220 | | | | |

| Leu | Ala | Ala | Ala | Gly | Val | Gln | Pro | His | Ser | Leu | Asp | Leu | Ser | His | Asn |
|---|---|---|---|---|---|---|---|---|---|---|---|---|---|---|---|
| 225 | | | | | 230 | | | | | 235 | | | | | 240 |

| Ser | Leu | Arg | Ala | Thr | Val | Asn | Pro | Ser | Ala | Pro | Arg | Cys | Met | Trp | Ser |
|---|---|---|---|---|---|---|---|---|---|---|---|---|---|---|---|
| | | | | 245 | | | | | 250 | | | | | 255 | |

| Ser | Ala | Leu | Asn | Ser | Leu | Asn | Leu | Ser | Phe | Ala | Gly | Leu | Glu | Gln | Val |
|---|---|---|---|---|---|---|---|---|---|---|---|---|---|---|---|
| | | | 260 | | | | | 265 | | | | | 270 | | |

| Pro | Lys | Gly | Leu | Pro | Ala | Lys | Leu | Arg | Val | Leu | Asp | Leu | Ser | Cys | Asn |
|---|---|---|---|---|---|---|---|---|---|---|---|---|---|---|---|
| | | 275 | | | | | 280 | | | | | 285 | | | |

| Arg | Leu | Asn | Arg | Ala | Pro | Gln | Pro | Asp | Glu | Leu | Pro | Glu | Val | Asp | Asn |
|---|---|---|---|---|---|---|---|---|---|---|---|---|---|---|---|
| | 290 | | | | | 295 | | | | | 300 | | | | |

| Leu | Thr | Leu | Asp | Gly | Asn | Pro | Phe | Leu | Val | Pro | Gly | Thr | Ala | Leu | Pro |
|---|---|---|---|---|---|---|---|---|---|---|---|---|---|---|---|
| 305 | | | | | 310 | | | | | 315 | | | | | 320 |

| His | Glu | Gly | Ser | Met | Asn | Ser | Gly | Val | Val | Pro | Ala | Cys | Ala | Arg | Ser |
|---|---|---|---|---|---|---|---|---|---|---|---|---|---|---|---|
| | | | | 325 | | | | | 330 | | | | | 335 | |

| Thr | Leu | Ser | Val | Gly | Val | Ser | Gly | Thr | Leu | Val | Leu |
|---|---|---|---|---|---|---|---|---|---|---|---|
| | | | 340 | | | | | 345 | | | |

( 2 ) INFORMATION FOR SEQ ID NO:8:

( i ) SEQUENCE CHARACTERISTICS:
    ( A ) LENGTH: 334 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:8:

| Cys | Val | Cys | Asn | Phe | Ser | Glu | Pro | Gln | Pro | Asp | Trp | Ser | Glu | Ala | Phe |
|---|---|---|---|---|---|---|---|---|---|---|---|---|---|---|---|
| 1 | | | | 5 | | | | | 10 | | | | | 15 | |

| Gln | Cys | Val | Ser | Ala | Val | Glu | Val | Glu | Ile | His | Ala | Gly | Gly | Leu | Asn |
|---|---|---|---|---|---|---|---|---|---|---|---|---|---|---|---|
| | | | 20 | | | | | 25 | | | | | 30 | | |

| Leu | Glu | Pro | Phe | Leu | Lys | Arg | Val | Asp | Ala | Asp | Ala | Asp | Pro | Arg | Gln |
|---|---|---|---|---|---|---|---|---|---|---|---|---|---|---|---|
| | | 35 | | | | | 40 | | | | 45 | | | | |

| Tyr | Ala | Asp | Thr | Val | Lys | Ala | Leu | Arg | Val | Arg | Arg | Leu | Thr | Val | Gly |
|---|---|---|---|---|---|---|---|---|---|---|---|---|---|---|---|
| | 50 | | | | | 55 | | | | | 60 | | | | |

| Ala | Ala | Gln | Val | Pro | Ala | Gln | Leu | Leu | Val | Gly | Ala | Leu | Arg | Val | Leu |
|---|---|---|---|---|---|---|---|---|---|---|---|---|---|---|---|
| 65 | | | | | 70 | | | | | 75 | | | | | 80 |

| Ala | Tyr | Ser | Arg | Leu | Lys | Glu | Leu | Thr | Leu | Glu | Asp | Leu | Lys | Ile | Thr |
|---|---|---|---|---|---|---|---|---|---|---|---|---|---|---|---|
| | | | | 85 | | | | | 90 | | | | | 95 | |

| Gly | Thr | Met | Pro | Pro | Leu | Pro | Leu | Glu | Ala | Thr | Gly | Leu | Ala | Leu | Ser |
|---|---|---|---|---|---|---|---|---|---|---|---|---|---|---|---|
| | | | 100 | | | | | 105 | | | | | 110 | | |

| Ser | Leu | Arg | Leu | Arg | Asn | Val | Ser | Trp | Ala | Thr | Gly | Arg | Ser | Trp | Leu |
|---|---|---|---|---|---|---|---|---|---|---|---|---|---|---|---|
| | | | 115 | | | | | 120 | | | | | 125 | | |

| Ala | Glu | Leu | Gln | Gln | Trp | Leu | Lys | Pro | Gly | Leu | Lys | Val | Leu | Ser | Ile |
|---|---|---|---|---|---|---|---|---|---|---|---|---|---|---|---|
| | | 130 | | | | | 135 | | | | | 140 | | | |

| Ala | Gln | Ala | His | Ser | Pro | Ala | Phe | Ser | Cys | Glu | Gln | Val | Arg | Ala | Phe |
|---|---|---|---|---|---|---|---|---|---|---|---|---|---|---|---|
| 145 | | | | | 150 | | | | | 155 | | | | | 160 |

| Pro | Ala | Leu | Thr | Ser | Leu | Asp | Leu | Ser | Asp | Asn | Pro | Gly | Leu | Gly | Glu |
|---|---|---|---|---|---|---|---|---|---|---|---|---|---|---|---|
| | | | | 165 | | | | | 170 | | | | | 175 | |

| Arg | Gly | Leu | Met | Ala | Ala | Leu | Cys | Pro | His | Lys | Phe | Pro | Ala | Ile | Gln |
|---|---|---|---|---|---|---|---|---|---|---|---|---|---|---|---|
| | | | 180 | | | | | 185 | | | | | 190 | | |

| Asn | Leu | Ala | Leu | Arg | Asn | Thr | Gly | Met | Glu | Thr | Pro | Thr | Gly | Val | Cys |
|---|---|---|---|---|---|---|---|---|---|---|---|---|---|---|---|
| | | 195 | | | | | 200 | | | | | 205 | | | |

| Ala | Ala | Leu | Ala | Ala | Ala | Gly | Val | Gln | Pro | His | Ser | Leu | Asp | Leu | Ser |
|---|---|---|---|---|---|---|---|---|---|---|---|---|---|---|---|
| | 210 | | | | | 215 | | | | | 220 | | | | |

| His | Asn | Ser | Leu | Arg | Ala | Thr | Val | Asn | Pro | Ser | Ala | Pro | Arg | Cys | Met |
|---|---|---|---|---|---|---|---|---|---|---|---|---|---|---|---|
| 225 | | | | | 230 | | | | | 235 | | | | | 240 |

| Trp | Ser | Ser | Ala | Leu | Asn | Ser | Leu | Asn | Leu | Ser | Phe | Ala | Gly | Leu | Glu |
|---|---|---|---|---|---|---|---|---|---|---|---|---|---|---|---|
| | | | | 245 | | | | | 250 | | | | | 255 | |

| Gln | Val | Pro | Lys | Gly | Leu | Pro | Ala | Lys | Leu | Arg | Val | Leu | Asp | Leu | Ser |
|---|---|---|---|---|---|---|---|---|---|---|---|---|---|---|---|
| | | | 260 | | | | | 265 | | | | | 270 | | |

| Cys | Asn | Arg | Leu | Asn | Arg | Ala | Pro | Gln | Pro | Asp | Glu | Leu | Pro | Glu | Val |
|---|---|---|---|---|---|---|---|---|---|---|---|---|---|---|---|
| | | 275 | | | | | 280 | | | | | 285 | | | |

| Asp | Asn | Leu | Thr | Leu | Asp | Gly | Asn | Pro | Phe | Leu | Val | Pro | Gly | Thr | Ala |
|---|---|---|---|---|---|---|---|---|---|---|---|---|---|---|---|
| | 290 | | | | | 295 | | | | | 300 | | | | |

| Leu | Pro | His | Glu | Gly | Ser | Met | Asn | Ser | Gly | Val | Val | Pro | Ala | Cys | Ala |
|---|---|---|---|---|---|---|---|---|---|---|---|---|---|---|---|
| 305 | | | | | 310 | | | | | 315 | | | | | 320 |

| Arg | Ser | Thr | Leu | Ser | Val | Gly | Val | Ser | Gly | Thr | Leu | Val | Leu |
|---|---|---|---|---|---|---|---|---|---|---|---|---|---|
| | | | | 325 | | | | | 330 | | | | |

( 2 ) INFORMATION FOR SEQ ID NO:9:

( i ) SEQUENCE CHARACTERISTICS:
        ( A ) LENGTH: 152 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

| Thr | Thr | Pro | Glu | Pro | Cys | Gly | Gly | Gly | Glu | Asp | Phe | Arg | Cys | Val |
|---|---|---|---|---|---|---|---|---|---|---|---|---|---|---|
| 1 | | | | 5 | | | | | 10 | | | | | 15 |

```
Cys  Asn  Phe  Ser  Glu  Pro  Gln  Pro  Asp  Trp  Ser  Glu  Ala  Phe  Gln  Cys
               20                  25                            30

Val  Ser  Ala  Val  Glu  Val  Glu  Ile  His  Ala  Gly  Gly  Leu  Asn  Leu  Glu
          35                       40                       45

Pro  Phe  Leu  Lys  Arg  Val  Asp  Ala  Asp  Ala  Asp  Pro  Arg  Gln  Tyr  Ala
     50                       55                       60

Asp  Thr  Val  Lys  Ala  Leu  Arg  Val  Arg  Arg  Leu  Thr  Val  Gly  Ala  Ala
65                            70                       75                      80

Gln  Val  Pro  Ala  Gln  Leu  Leu  Val  Gly  Ala  Leu  Arg  Val  Leu  Ala  Tyr
                    85                       90                            95

Ser  Arg  Leu  Lys  Glu  Leu  Thr  Leu  Glu  Asp  Leu  Lys  Ile  Thr  Gly  Thr
               100                      105                      110

Met  Pro  Pro  Leu  Pro  Leu  Glu  Ala  Thr  Gly  Leu  Ala  Leu  Ser  Ser  Leu
          115                      120                      125

Arg  Leu  Arg  Asn  Val  Ser  Trp  Ala  Thr  Gly  Arg  Ser  Trp  Leu  Ala  Glu
     130                      135                      140

Leu  Gln  Gln  Trp  Leu  Lys  Pro  Gly
145                      150
```

( 2 ) INFORMATION FOR SEQ ID NO:10:

( i ) SEQUENCE CHARACTERISTICS:
        ( A ) LENGTH: 152 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Thr  Thr  Pro  Glu  Pro  Cys  Ala  Ala  Ala  Glu  Asp  Phe  Arg  Cys  Val
1                   5                        10                      15

Cys  Asn  Phe  Ser  Glu  Pro  Gln  Pro  Asp  Trp  Ser  Glu  Ala  Phe  Gln  Cys
               20                  25                            30

Val  Ser  Ala  Val  Glu  Val  Glu  Ile  His  Ala  Gly  Gly  Leu  Asn  Leu  Glu
          35                       40                       45

Pro  Phe  Leu  Lys  Arg  Val  Asp  Ala  Asp  Ala  Asp  Pro  Arg  Gln  Tyr  Ala
     50                       55                       60

Asp  Thr  Val  Lys  Ala  Leu  Arg  Val  Arg  Arg  Leu  Thr  Val  Gly  Ala  Ala
65                            70                       75                      80

Gln  Val  Pro  Ala  Gln  Leu  Leu  Val  Gly  Ala  Leu  Arg  Val  Leu  Ala  Tyr
                    85                       90                            95

Ser  Arg  Leu  Lys  Glu  Leu  Thr  Leu  Glu  Asp  Leu  Lys  Ile  Thr  Gly  Thr
               100                      105                      110

Met  Pro  Pro  Leu  Pro  Leu  Glu  Ala  Thr  Gly  Leu  Ala  Leu  Ser  Ser  Leu
          115                      120                      125

Arg  Leu  Arg  Asn  Val  Ser  Trp  Ala  Thr  Gly  Arg  Ser  Trp  Leu  Ala  Glu
     130                      135                      140

Leu  Gln  Gln  Trp  Leu  Lys  Pro  Gly
145                      150
```

( 2 ) INFORMATION FOR SEQ ID NO:11:

( i ) SEQUENCE CHARACTERISTICS:
        ( A ) LENGTH: 152 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

| Thr | Thr | Pro | Glu | Pro | Cys | Val | Val | Val | Glu | Asp | Phe | Arg | Cys | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Cys | Asn | Phe | Ser | Glu | Pro | Gln | Pro | Asp | Trp | Ser | Glu | Ala | Phe | Gln | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Ser | Ala | Val | Glu | Val | Glu | Ile | His | Ala | Gly | Gly | Leu | Asn | Leu | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Pro | Phe | Leu | Lys | Arg | Val | Asp | Ala | Asp | Ala | Asp | Pro | Arg | Gln | Tyr | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asp | Thr | Val | Lys | Ala | Leu | Arg | Val | Arg | Arg | Leu | Thr | Val | Gly | Ala | Ala |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Val | Pro | Ala | Gln | Leu | Leu | Val | Gly | Ala | Leu | Arg | Val | Leu | Ala | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Arg | Leu | Lys | Glu | Leu | Thr | Leu | Glu | Asp | Leu | Lys | Ile | Thr | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Met | Pro | Pro | Leu | Pro | Leu | Glu | Ala | Thr | Gly | Leu | Ala | Leu | Ser | Ser | Leu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Arg | Leu | Arg | Asn | Val | Ser | Trp | Ala | Thr | Gly | Arg | Ser | Trp | Leu | Ala | Glu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Leu | Gln | Gln | Trp | Leu | Lys | Pro | Gly |
|-----|-----|-----|-----|-----|-----|-----|-----|
| 145 |     |     |     |     | 150 |     |     |

( 2 ) INFORMATION FOR SEQ ID NO:12:

( i ) SEQUENCE CHARACTERISTICS:
        ( A ) LENGTH: 152 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

| Thr | Thr | Pro | Glu | Pro | Cys | Leu | Leu | Leu | Glu | Asp | Phe | Arg | Cys | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Cys | Asn | Phe | Ser | Glu | Pro | Gln | Pro | Asp | Trp | Ser | Glu | Ala | Phe | Gln | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Ser | Ala | Val | Glu | Val | Glu | Ile | His | Ala | Gly | Gly | Leu | Asn | Leu | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Pro | Phe | Leu | Lys | Arg | Val | Asp | Ala | Asp | Ala | Asp | Pro | Arg | Gln | Tyr | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asp | Thr | Val | Lys | Ala | Leu | Arg | Val | Arg | Arg | Leu | Thr | Val | Gly | Ala | Ala |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Val | Pro | Ala | Gln | Leu | Leu | Val | Gly | Ala | Leu | Arg | Val | Leu | Ala | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Arg | Leu | Lys | Glu | Leu | Thr | Leu | Glu | Asp | Leu | Lys | Ile | Thr | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Met | Pro | Pro | Leu | Pro | Leu | Glu | Ala | Thr | Gly | Leu | Ala | Leu | Ser | Ser | Leu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Arg | Leu | Arg | Asn | Val | Ser | Trp | Ala | Thr | Gly | Arg | Ser | Trp | Leu | Ala | Glu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Leu | Gln | Gln | Trp | Leu | Lys | Pro | Gly |
|-----|-----|-----|-----|-----|-----|-----|-----|
| 145 |     |     |     |     | 150 |     |     |

( 2 ) INFORMATION FOR SEQ ID NO:13:

( i ) SEQUENCE CHARACTERISTICS:
 ( A ) LENGTH: 152 amino acids
 ( B ) TYPE: amino acid
 ( C ) STRANDEDNESS: single
 ( D ) TOPOLOGY: linear ( i i ) MOLECULE TYPE: protein ( x i ) SEQUENCE DESCRIPTION: SEQ ID NO:13:

```
Thr  Thr  Pro  Glu  Pro  Cys  Ile  Ile  Ile  Ile  Glu  Asp  Phe  Arg  Cys  Val
 1              5                        10                            15

Cys  Asn  Phe  Ser  Glu  Pro  Gln  Pro  Asp  Trp  Ser  Glu  Ala  Phe  Gln  Cys
               20                       25                       30

Val  Ser  Ala  Val  Glu  Val  Glu  Ile  His  Ala  Gly  Gly  Leu  Asn  Leu  Glu
          35                        40                       45

Pro  Phe  Leu  Lys  Arg  Val  Asp  Ala  Asp  Ala  Asp  Pro  Arg  Gln  Tyr  Ala
     50                        55                       60

Asp  Thr  Val  Lys  Ala  Leu  Arg  Val  Arg  Arg  Leu  Thr  Val  Gly  Ala  Ala
 65                       70                       75                        80

Gln  Val  Pro  Ala  Gln  Leu  Leu  Val  Gly  Ala  Leu  Arg  Val  Leu  Ala  Tyr
                    85                       90                       95

Ser  Arg  Leu  Lys  Glu  Leu  Thr  Leu  Glu  Asp  Leu  Lys  Ile  Thr  Gly  Thr
               100                      105                     110

Met  Pro  Pro  Leu  Pro  Leu  Glu  Ala  Thr  Gly  Leu  Ala  Leu  Ser  Ser  Leu
               115                      120                     125

Arg  Leu  Arg  Asn  Val  Ser  Trp  Ala  Thr  Gly  Arg  Ser  Trp  Leu  Ala  Glu
          130                      135                     140

Leu  Gln  Gln  Trp  Leu  Lys  Pro  Gly
145                      150
```

( 2 ) INFORMATION FOR SEQ ID NO:14:

( i ) SEQUENCE CHARACTERISTICS:
 ( A ) LENGTH: 152 amino acids
 ( B ) TYPE: amino acid
 ( C ) STRANDEDNESS: single
 ( D ) TOPOLOGY: linear ( i i ) MOLECULE TYPE: protein ( x i ) SEQUENCE DESCRIPTION: SEQ ID NO:14:

```
Thr  Thr  Pro  Glu  Pro  Cys  Pro  Pro  Pro  Glu  Asp  Phe  Arg  Cys  Val
 1              5                        10                            15

Cys  Asn  Phe  Ser  Glu  Pro  Gln  Pro  Asp  Trp  Ser  Glu  Ala  Phe  Gln  Cys
               20                       25                       30

Val  Ser  Ala  Val  Glu  Val  Glu  Ile  His  Ala  Gly  Gly  Leu  Asn  Leu  Glu
          35                        40                       45

Pro  Phe  Leu  Lys  Arg  Val  Asp  Ala  Asp  Ala  Asp  Pro  Arg  Gln  Tyr  Ala
     50                        55                       60

Asp  Thr  Val  Lys  Ala  Leu  Arg  Val  Arg  Arg  Leu  Thr  Val  Gly  Ala  Ala
 65                       70                       75                        80

Gln  Val  Pro  Ala  Gln  Leu  Leu  Val  Gly  Ala  Leu  Arg  Val  Leu  Ala  Tyr
                    85                       90                       95

Ser  Arg  Leu  Lys  Glu  Leu  Thr  Leu  Glu  Asp  Leu  Lys  Ile  Thr  Gly  Thr
               100                      105                     110

Met  Pro  Pro  Leu  Pro  Leu  Glu  Ala  Thr  Gly  Leu  Ala  Leu  Ser  Ser  Leu
               115                      120                     125

Arg  Leu  Arg  Asn  Val  Ser  Trp  Ala  Thr  Gly  Arg  Ser  Trp  Leu  Ala  Glu
          130                      135                     140
```

```
        Leu  Gln  Gln  Trp  Leu  Lys  Pro  Gly
        145                 150
```

( 2 ) INFORMATION FOR SEQ ID NO:15:

( i ) SEQUENCE CHARACTERISTICS:
        ( A ) LENGTH: 138 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Cys  Val  Cys  Asn  Phe  Ser  Glu  Pro  Gln  Pro  Asp  Trp  Ser  Glu  Ala  Phe
1                   5                   10                  15
Gln  Cys  Val  Ser  Ala  Val  Glu  Val  Glu  Ile  His  Ala  Gly  Gly  Leu  Asn
                    20                  25                  30
Leu  Glu  Pro  Phe  Leu  Lys  Arg  Val  Asp  Ala  Asp  Ala  Asp  Pro  Arg  Gln
                35                  40                  45
Tyr  Ala  Asp  Thr  Val  Lys  Ala  Leu  Arg  Val  Arg  Arg  Leu  Thr  Val  Gly
          50                  55                  60
Ala  Ala  Gln  Val  Pro  Ala  Gln  Leu  Leu  Val  Gly  Ala  Leu  Arg  Val  Leu
65                  70                  75                  80
Ala  Tyr  Ser  Arg  Leu  Lys  Glu  Leu  Thr  Leu  Glu  Asp  Leu  Lys  Ile  Thr
                    85                  90                  95
Gly  Thr  Met  Pro  Pro  Leu  Pro  Leu  Glu  Ala  Thr  Gly  Leu  Ala  Leu  Ser
                100                 105                 110
Ser  Leu  Arg  Leu  Arg  Asn  Val  Ser  Trp  Ala  Thr  Gly  Arg  Ser  Trp  Leu
          115                 120                 125
Ala  Glu  Leu  Gln  Gln  Trp  Leu  Lys  Pro  Gly
130                 135
```

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CGCCAGAACC TTGTGCAGCT GCCGCTGAAG ATTTCCGCTG C        41

( 2 ) INFORMATION FOR SEQ ID NO:17:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GTGAGCTGGA CGATGCAGCT GCCGCCTGCG TCTGCAACTT C        41

( 2 ) INFORMATION FOR SEQ ID NO:18:

( i ) SEQUENCE CHARACTERISTICS:
        ( A ) LENGTH: 40 base pairs
        ( B ) TYPE: nucleic acid
        ( C ) STRANDEDNESS: single (D) TOPOLOGY: linear (i i) MOLECULE TYPE: cDNA (x i) SEQUENCE DESCRIPTION: SEQ ID NO:18:

CCGCTGCGTC TGCGCAGCTG CCGCACCTCA GCCCGACTGG 40

(2) INFORMATION FOR SEQ ID NO:19:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:19:

GCAACTTCTC CGAAGCAGCT GCCGCCTGGT CCGAAGCCTT C 41

(2) INFORMATION FOR SEQ ID NO:20:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:20:

GAACCTCAGC CCGACGCAGC TGCAGCCTTC CAGTGTGTG 39

(2) INFORMATION FOR SEQ ID NO:21:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:21:

CCGACTGGTC CGAAGCAGCT GCGTGTGTGT CTGCAGTAGA G 41

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:22:

CATGCCGGCG GTGCAGCTGC AGCGCCGTTT CTAAAGCGCG 40

(2) INFORMATION FOR SEQ ID NO:23:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:23:

GGTCTCAACC TAGAGGCAGC TGCAGCGCGC GTCGATGCGG AC                                    42

( 2 ) INFORMATION FOR SEQ ID NO:24:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

GAGCCGTTTC TAAAGGCAGC TGCTGCGGAC GCCGACCCG                                        39

( 2 ) INFORMATION FOR SEQ ID NO:25:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

CATGGAGGGA CTTTCCGCTG GGGACTTTCC AGC                                              33

( 2 ) INFORMATION FOR SEQ ID NO:26:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CATGGCTGGA AAGTCCCCAG CGGAAAGTCC CTC                                              33

( 2 ) INFORMATION FOR SEQ ID NO:27:

( i ) SEQUENCE CHARACTERISTICS:
        ( A ) LENGTH: 348 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

```
Thr Thr Pro Glu Pro Cys Glu Leu Asp Asp Glu Asp Phe Arg Cys Val
 1               5                  10                  15
Cys Asn Phe Ser Glu Pro Gln Pro Asp Trp Ser Glu Ala Phe Gln Cys
                20                  25                  30
Val Ser Ala Val Glu Val Glu Ile His Ala Gly Gly Leu Asn Leu Glu
                35                  40                  45
Pro Phe Leu Lys Arg Val Asp Ala Asp Ala Asp Pro Arg Gln Tyr Ala
        50                  55                  60
Asp Thr Val Lys Ala Leu Arg Val Arg Arg Leu Thr Val Gly Ala Ala
65                  70                  75                  80
Gln Val Pro Ala Gln Leu Leu Val Gly Ala Leu Arg Val Leu Ala Tyr
                85                  90                  95
Ser Arg Leu Lys Glu Leu Thr Leu Glu Asp Leu Lys Ile Thr Gly Thr
```

|     |     |     |     |     |     | 100 |     |     |     | 105 |     |     |     | 110 |     |
| --- | --- | --- | --- | --- | --- | --- | --- | --- | --- | --- | --- | --- | --- | --- | --- |
| Met | Pro | Pro | Leu | Pro | Leu | Glu | Ala | Thr | Gly | Leu | Ala | Leu | Ser | Ser | Leu |
|     |     | 115 |     |     |     | 120 |     |     |     | 125 |     |     |     |     |     |
| Arg | Leu | Arg | Asn | Val | Ser | Trp | Ala | Thr | Gly | Arg | Ser | Trp | Leu | Ala | Glu |
|     | 130 |     |     |     |     | 135 |     |     |     | 140 |     |     |     |     |     |
| Leu | Gln | Gln | Trp | Leu | Lys | Pro | Gly | Leu | Lys | Val | Leu | Ser | Ile | Ala | Gln |
| 145 |     |     |     |     | 150 |     |     |     |     | 155 |     |     |     |     | 160 |
| Ala | His | Ser | Pro | Ala | Phe | Ser | Cys | Glu | Gln | Val | Arg | Ala | Phe | Pro | Ala |
|     |     |     |     | 165 |     |     |     |     | 170 |     |     |     |     | 175 |     |
| Leu | Thr | Ser | Leu | Asp | Leu | Ser | Asp | Asn | Pro | Gly | Leu | Gly | Glu | Arg | Gly |
|     |     |     |     | 180 |     |     |     |     | 185 |     |     |     |     | 190 |     |
| Leu | Met | Ala | Ala | Leu | Cys | Pro | His | Lys | Phe | Pro | Ala | Ile | Gln | Asn | Leu |
|     |     | 195 |     |     |     |     | 200 |     |     |     |     | 205 |     |     |     |
| Ala | Leu | Arg | Asn | Thr | Gly | Met | Glu | Thr | Pro | Thr | Gly | Val | Cys | Ala | Ala |
|     | 210 |     |     |     |     | 215 |     |     |     |     | 220 |     |     |     |     |
| Leu | Ala | Ala | Ala | Gly | Val | Gln | Pro | His | Ser | Leu | Asp | Leu | Ser | His | Asn |
| 225 |     |     |     |     | 230 |     |     |     |     | 235 |     |     |     |     | 240 |
| Ser | Leu | Arg | Ala | Thr | Val | Asn | Pro | Ser | Ala | Pro | Arg | Cys | Met | Trp | Ser |
|     |     |     |     | 245 |     |     |     |     | 250 |     |     |     |     | 255 |     |
| Ser | Ala | Leu | Asn | Ser | Leu | Asn | Leu | Ser | Phe | Ala | Gly | Leu | Glu | Gln | Val |
|     |     |     | 260 |     |     |     |     | 265 |     |     |     |     | 270 |     |     |
| Pro | Lys | Gly | Leu | Pro | Ala | Lys | Leu | Arg | Val | Leu | Asp | Leu | Ser | Cys | Asn |
|     |     | 275 |     |     |     |     | 280 |     |     |     |     | 285 |     |     |     |
| Arg | Leu | Asn | Arg | Ala | Pro | Gln | Pro | Asp | Glu | Leu | Pro | Glu | Val | Asp | Asn |
|     | 290 |     |     |     |     | 295 |     |     |     |     | 300 |     |     |     |     |
| Leu | Thr | Leu | Asp | Gly | Asn | Pro | Phe | Leu | Val | Pro | Gly | Thr | Ala | Leu | Pro |
| 305 |     |     |     |     | 310 |     |     |     |     | 315 |     |     |     |     | 320 |
| His | Glu | Gly | Ser | Met | Asn | Ser | Gly | Val | Val | Pro | Ala | Cys | Ala | Arg | Ser |
|     |     |     |     | 325 |     |     |     |     | 330 |     |     |     |     | 335 |     |
| Thr | Leu | Ser | Val | Gly | Val | Ser | Gly | Thr | Leu | Val | Leu |     |     |     |     |
|     |     |     | 340 |     |     |     |     | 345 |     |     |     |     |     |     |     |

( 2 ) INFORMATION FOR SEQ ID NO:28:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

| Thr | Thr | Pro | Glu | Pro | Cys | Glu | Leu | Asp | Asp | Glu | Asp | Phe | Arg | Cys | Val |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Cys | Asn | Phe | Ser | Glu | Pro | Gln | Pro | Asp | Trp | Ser | Glu | Ala | Phe | Gln | Cys |
|     |     |     | 20  |     |     |     |     | 25  |     |     |     |     | 30  |     |     |
| Val | Ser | Ala | Val | Glu | Val | Glu | Ile | His | Ala | Gly | Gly | Leu | Asn | Leu | Glu |
|     |     | 35  |     |     |     |     | 40  |     |     |     |     | 45  |     |     |     |
| Pro | Phe | Leu | Lys | Arg | Val | Asp | Ala | Asp | Ala | Asp | Pro |     |     |     |     |
|     | 50  |     |     |     |     | 55  |     |     |     |     | 60  |     |     |     |     |

( 2 ) INFORMATION FOR SEQ ID NO:29:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:29:

```
Thr Thr Pro Glu Pro Cys Ala Ala Ala Ala Glu Asp Phe Arg Cys Val
1               5                   10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro
    50                  55                  60
```

(2) INFORMATION FOR SEQ ID NO:30:

(i) SEQUENCE CHARACTERISTICS:
        (A) LENGTH: 60 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:30:

```
Thr Thr Pro Glu Pro Cys Glu Leu Asp Asp Ala Ala Ala Ala Cys Val
1               5                   10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro
    50                  55                  60
```

(2) INFORMATION FOR SEQ ID NO:31:

(i) SEQUENCE CHARACTERISTICS:
        (A) LENGTH: 60 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:31:

```
Thr Thr Pro Glu Pro Cys Glu Leu Asp Asp Glu Asp Phe Arg Cys Val
1               5                   10                  15

Cys Ala Ala Ala Ala Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro
    50                  55                  60
```

(2) INFORMATION FOR SEQ ID NO:32:

(i) SEQUENCE CHARACTERISTICS:
        (A) LENGTH: 60 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:32:

-continued

```
Thr Thr Pro Glu Pro Cys Glu Leu Asp Asp Glu Asp Phe Arg Cys Val
 1               5                      10                      15

Cys Asn Phe Ser Glu Ala Ala Ala Trp Ser Glu Ala Phe Gln Cys
                 20              25                  30

Val Ser Ala Val Glu Val Glu Ile His Ala Gly Gly Leu Asn Leu Glu
             35                  40                      45

Pro Phe Leu Lys Arg Val Asp Ala Asp Ala Asp Pro
 50                      55                  60
```

(2) INFORMATION FOR SEQ ID NO:33:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Thr Thr Pro Glu Pro Cys Glu Leu Asp Asp Glu Asp Phe Arg Cys Val
 1               5                      10                      15

Cys Asn Phe Ser Glu Pro Gln Pro Asp Ala Ala Ala Ala Phe Gln Cys
                 20              25                  30

Val Ser Ala Val Glu Val Glu Ile His Ala Gly Gly Leu Asn Leu Glu
             35                  40                      45

Pro Phe Leu Lys Arg Val Asp Ala Asp Ala Asp Pro
 50                      55                  60
```

(2) INFORMATION FOR SEQ ID NO:34:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

```
Thr Thr Pro Glu Pro Cys Glu Leu Asp Asp Glu Asp Phe Arg Cys Val
 1               5                      10                      15

Cys Asn Phe Ser Glu Pro Gln Pro Asp Trp Ser Glu Ala Ala Ala Cys
                 20              25                  30

Val Ser Ala Val Glu Val Glu Ile His Ala Gly Gly Leu Asn Leu Glu
             35                  40                      45

Pro Phe Leu Lys Arg Val Asp Ala Asp Ala Asp Pro
 50                      55                  60
```

(2) INFORMATION FOR SEQ ID NO:35:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Thr Thr Pro Glu Pro Cys Glu Leu Asp Asp Glu Asp Phe Arg Cys Val
 1               5                      10                      15

Cys Asn Phe Ser Glu Pro Gln Pro Asp Trp Ser Glu Ala Phe Gln Cys
                 20              25                  30
```

|   |   |   |   |   |   |   |   |   |   |   |   |   |   |   |
|---|---|---|---|---|---|---|---|---|---|---|---|---|---|---|
| Val | Ser | Ala | Val | Glu | Val | Glu | Ile | His | Ala | Gly | Gly | Ala | Ala | Ala | Ala |
|   |   | 35 |   |   |   | 40 |   |   |   |   | 45 |   |   |   |
| Pro | Phe | Leu | Lys | Arg | Val | Asp | Ala | Asp | Ala | Asp | Pro |
|   |   | 50 |   |   |   | 55 |   |   |   |   | 60 |

(2) INFORMATION FOR SEQ ID NO:36:

(i) SEQUENCE CHARACTERISTICS:
    (A) LENGTH: 60 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:36:

| Thr | Thr | Pro | Glu | Pro | Cys | Glu | Leu | Asp | Asp | Glu | Asp | Phe | Arg | Cys | Val |
|---|---|---|---|---|---|---|---|---|---|---|---|---|---|---|---|
| 1 |   |   |   | 5 |   |   |   |   | 10 |   |   |   |   | 15 |

| Cys | Asn | Phe | Ser | Glu | Pro | Gln | Pro | Asp | Trp | Ser | Glu | Ala | Phe | Gln | Cys |
|   |   |   | 20 |   |   |   |   | 25 |   |   |   |   | 30 |

| Val | Ser | Ala | Val | Glu | Val | Glu | Ile | His | Ala | Gly | Gly | Leu | Asn | Leu | Glu |
|   |   | 35 |   |   |   | 40 |   |   |   |   | 45 |

| Ala | Ala | Ala | Ala | Arg | Val | Asp | Ala | Asp | Ala | Asp | Pro |
|   |   | 50 |   |   |   | 55 |   |   |   |   | 60 |

(2) INFORMATION FOR SEQ ID NO:37:

(i) SEQUENCE CHARACTERISTICS:
    (A) LENGTH: 60 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:37:

| Thr | Thr | Pro | Glu | Pro | Cys | Glu | Leu | Asp | Asp | Glu | Asp | Phe | Arg | Cys | Val |
|---|---|---|---|---|---|---|---|---|---|---|---|---|---|---|---|
| 1 |   |   |   | 5 |   |   |   |   | 10 |   |   |   |   | 15 |

| Cys | Asn | Phe | Ser | Glu | Pro | Gln | Pro | Asp | Trp | Ser | Glu | Ala | Phe | Gln | Cys |
|   |   |   | 20 |   |   |   |   | 25 |   |   |   |   | 30 |

| Val | Ser | Ala | Val | Glu | Val | Glu | Ile | His | Ala | Gly | Gly | Leu | Asn | Leu | Glu |
|   |   | 35 |   |   |   | 40 |   |   |   |   | 45 |

| Pro | Phe | Leu | Lys | Ala | Ala | Ala | Ala | Asp | Ala | Asp | Pro |
|   |   | 50 |   |   |   | 55 |   |   |   |   | 60 |

(2) INFORMATION FOR SEQ ID NO:38:

(i) SEQUENCE CHARACTERISTICS:
    (A) LENGTH: 348 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Modified-site
    (B) LOCATION: 7..10
    (D) OTHER INFORMATION: /product="OTHER"
        / label= Xaa
        / note= "Xaa is independently selected from Gly, Ala, Val,
        Ile and Pro"

(xi) SEQUENCE DESCRIPTION: SEQ ID NO:38:

| Thr | Thr | Pro | Glu | Pro | Cys | Xaa | Xaa | Xaa | Xaa | Glu | Asp | Phe | Arg | Cys | Val |
|---|---|---|---|---|---|---|---|---|---|---|---|---|---|---|---|
| 1 |   |   |   | 5 |   |   |   |   | 10 |   |   |   |   | 15 |

-continued

```
Cys Asn Phe Ser Glu Pro Gln Pro Asp Trp Ser Glu Ala Phe Gln Cys
            20                      25                      30
Val Ser Ala Val Glu Val Glu Ile His Ala Gly Gly Leu Asn Leu Glu
        35                  40                      45
Pro Phe Leu Lys Arg Val Asp Ala Asp Ala Asp Pro Arg Gln Tyr Ala
    50                      55                  60
Asp Thr Val Lys Ala Leu Arg Val Arg Arg Leu Thr Val Gly Ala Ala
65                      70                  75                  80
Gln Val Pro Ala Gln Leu Leu Val Gly Ala Leu Arg Val Leu Ala Tyr
                85                  90                      95
Ser Arg Leu Lys Glu Leu Thr Leu Glu Asp Leu Lys Ile Thr Gly Thr
            100                     105                 110
Met Pro Pro Leu Pro Leu Glu Ala Thr Gly Leu Ala Leu Ser Ser Leu
            115                 120                 125
Arg Leu Arg Asn Val Ser Trp Ala Thr Gly Arg Ser Trp Leu Ala Glu
        130                 135                 140
Leu Gln Gln Trp Leu Lys Pro Gly Leu Lys Val Leu Ser Ile Ala Gln
145                     150                 155                 160
Ala His Ser Pro Ala Phe Ser Cys Glu Gln Val Arg Ala Phe Pro Ala
                165                 170                 175
Leu Thr Ser Leu Asp Leu Ser Asp Asn Pro Gly Leu Gly Glu Arg Gly
            180                 185                 190
Leu Met Ala Ala Leu Cys Pro His Lys Phe Pro Ala Ile Gln Asn Leu
        195                 200                 205
Ala Leu Arg Asn Thr Gly Met Glu Thr Pro Thr Gly Val Cys Ala Ala
    210                 215                 220
Leu Ala Ala Ala Gly Val Gln Pro His Ser Leu Asp Leu Ser His Asn
225                 230                 235                     240
Ser Leu Arg Ala Thr Val Asn Pro Ser Ala Pro Arg Cys Met Trp Ser
                245                 250                 255
Ser Ala Leu Asn Ser Leu Asn Leu Ser Phe Ala Gly Leu Glu Gln Val
            260                 265                 270
Pro Lys Gly Leu Pro Ala Lys Leu Arg Val Leu Asp Leu Ser Cys Asn
        275                 280                 285
Arg Leu Asn Arg Ala Pro Gln Pro Asp Glu Leu Pro Glu Val Asp Asn
    290                 295                 300
Leu Thr Leu Asp Gly Asn Pro Phe Leu Val Pro Gly Thr Ala Leu Pro
305                 310                 315                 320
His Glu Gly Ser Met Asn Ser Gly Val Val Pro Ala Cys Ala Arg Ser
                325                 330                 335
Thr Leu Ser Val Gly Val Ser Gly Thr Leu Val Leu
            340                 345
```